US008668661B2

(12) United States Patent  
Mueller et al.

(10) Patent No.: US 8,668,661 B2
(45) Date of Patent: Mar. 11, 2014

(54) KNEE BRACE

(75) Inventors: Brett Mueller, Middleton, WI (US); Eric D. Bybee, Merrimac, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 1585 days.

(21) Appl. No.: 11/556,684

(22) Filed: Nov. 3, 2006

(65) Prior Publication Data

US 2007/0106191 A1    May 10, 2007

Related U.S. Application Data

(60) Provisional application No. 60/733,374, filed on Nov. 4, 2005, provisional application No. 60/763,190, filed on Jan. 28, 2006.

(51) Int. Cl.
*A61F 5/00* (2006.01)

(52) U.S. Cl.
USPC ............... 602/26; 602/23; 602/60; 602/61; 602/62

(58) Field of Classification Search
USPC .............. 602/26, 1, 3, 5, 23, 14, 60–62, 63; 128/882; 2/22, 24, 911
See application file for complete search history.

(56) References Cited

U.S. PATENT DOCUMENTS

| | | | |
|---|---|---|---|
| 4,219,892 A * | 9/1980 | Rigdon | 2/24 |
| 4,287,885 A * | 9/1981 | Applegate | 602/26 |
| 4,353,362 A | 10/1982 | DeMarco | |
| 4,366,813 A * | 1/1983 | Nelson | 602/26 |
| 5,016,621 A | 5/1991 | Bender | |
| 5,139,477 A | 8/1992 | Peters | |
| 5,399,153 A * | 3/1995 | Caprio et al. | 602/26 |
| 5,626,557 A * | 5/1997 | Mann | 602/26 |
| 5,658,241 A | 8/1997 | Deharde et al. | |
| 5,823,981 A * | 10/1998 | Grim et al. | 602/26 |
| D501,927 S | 2/2005 | McCormick et al. | |
| 7,083,586 B2 | 8/2006 | Simmons et al. | |
| D527,825 S | 9/2006 | Ingimundarson et al. | |
| 7,217,249 B2 | 5/2007 | Scott | |
| 2004/0153017 A1* | 8/2004 | Simmons et al. | 602/26 |
| 2004/0176715 A1* | 9/2004 | Nelson | 602/26 |
| 2005/0240134 A1* | 10/2005 | Brown | 602/26 |
| 2006/0030802 A1* | 2/2006 | Nordt et al. | 602/26 |
| 2006/0135903 A1 | 6/2006 | Ingimundarson et al. | |

FOREIGN PATENT DOCUMENTS

WO    DM/052483    9/2000

* cited by examiner

*Primary Examiner* — Patricia Bianco
*Assistant Examiner* — Keri J Nelson
(74) *Attorney, Agent, or Firm* — Rick L. Abegglen

(57) ABSTRACT

A knee brace, for use by athletes or others requiring protection and support of the knee, that includes an elastic base that covers the knee and adjacent portions of the leg of a person, a mesh support layer covering an upper portion of the base and extending below the knee when the brace is worn, and a below-knee support panel made of an inelastic sheet material. The mesh support layer can have a symmetric construction, and can have overlapping ears, although this is not required. Alternative embodiments of a knee brace according to the present invention can include a mesh support layer that covers the patella tendon, or a mesh support layer that encircles the kneecap.

31 Claims, 25 Drawing Sheets

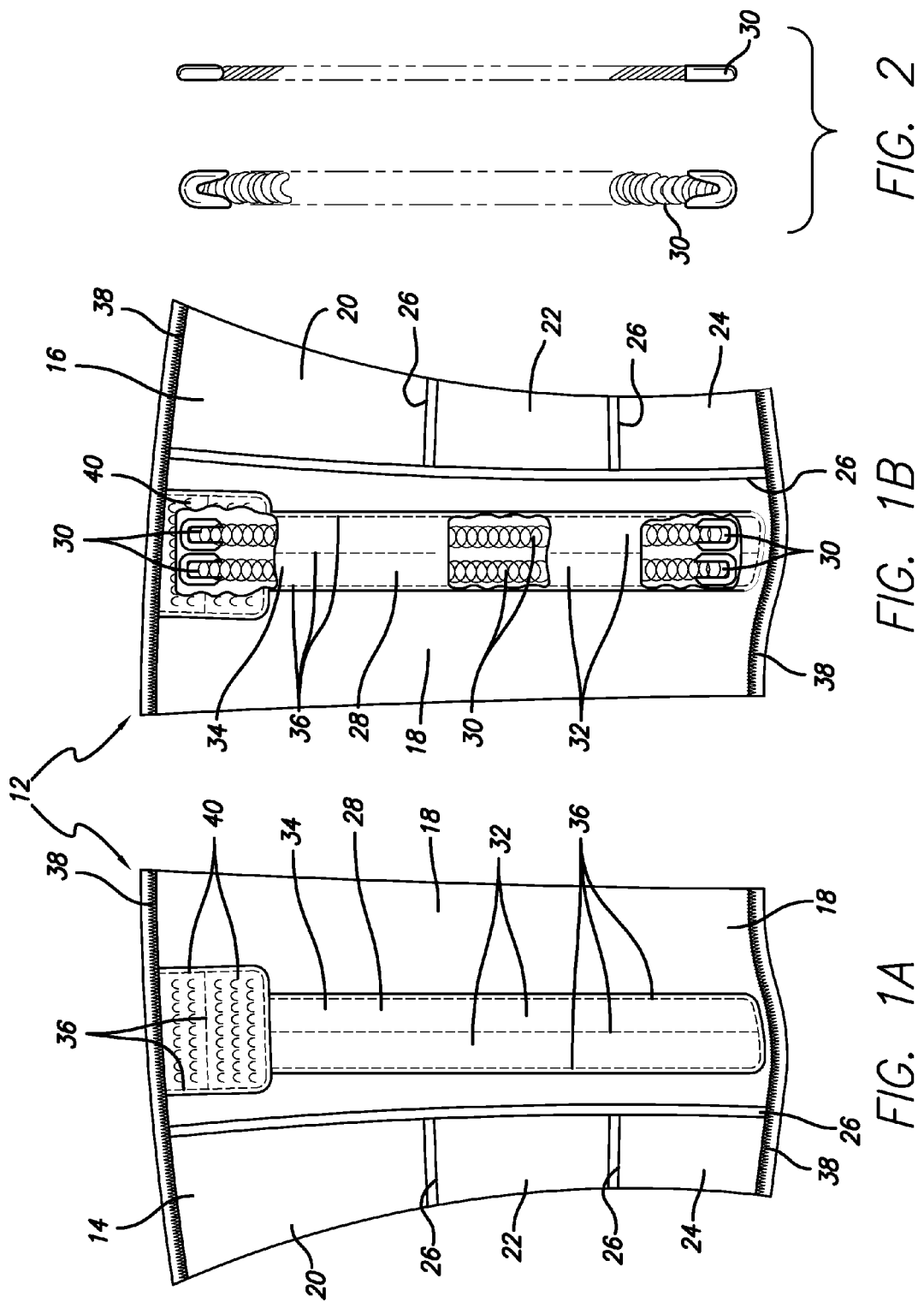

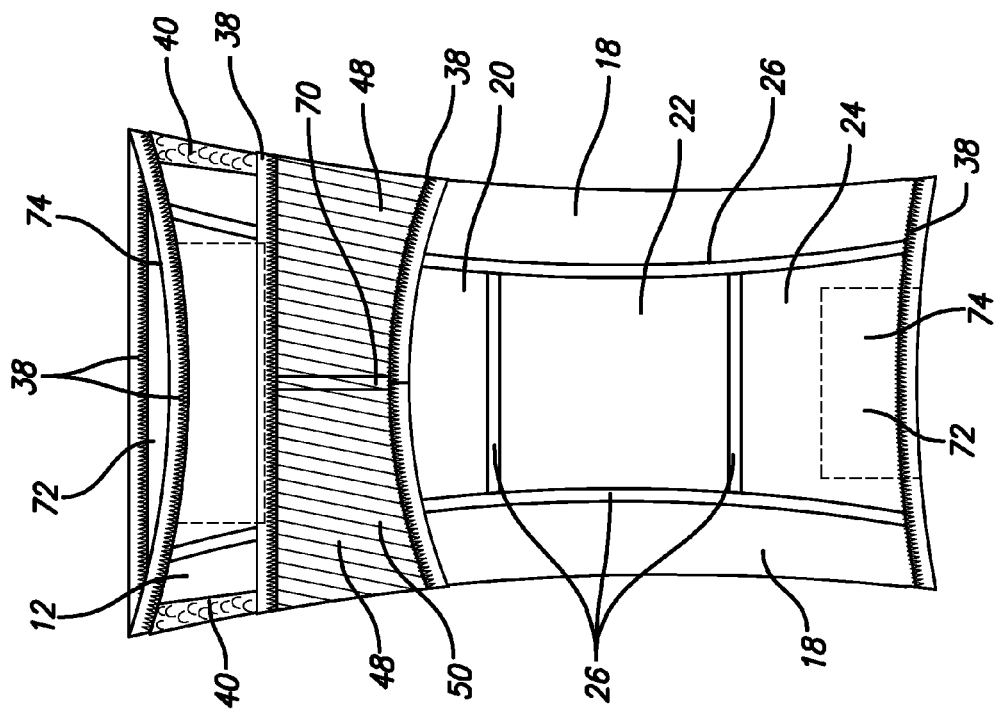
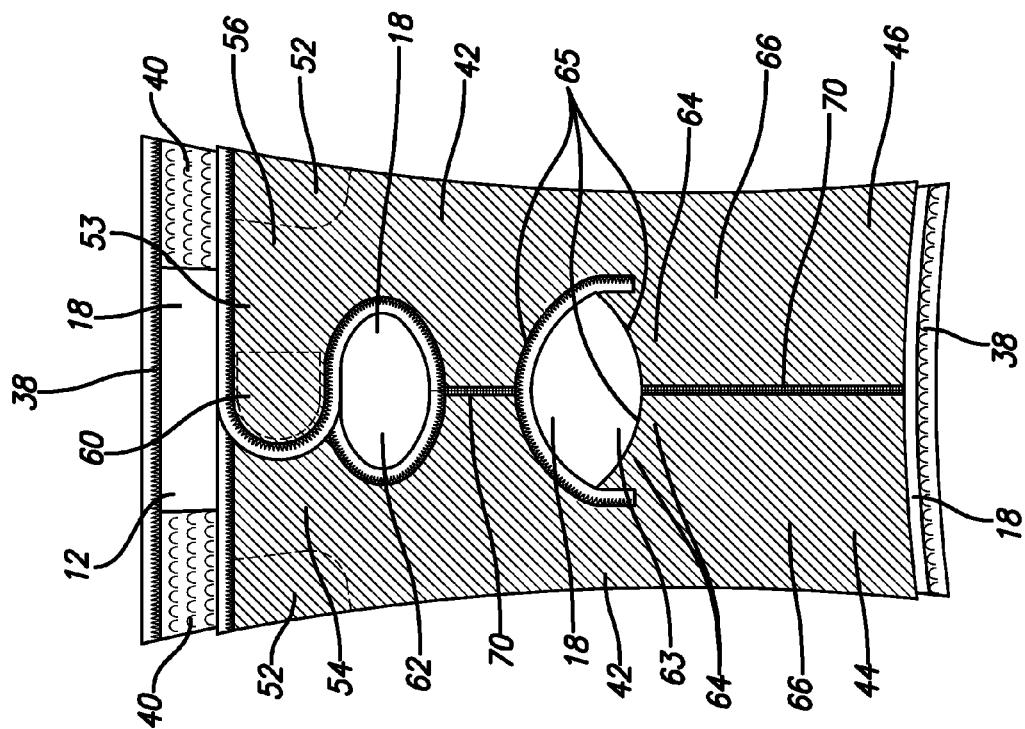
FIG. 3B
FIG. 3A

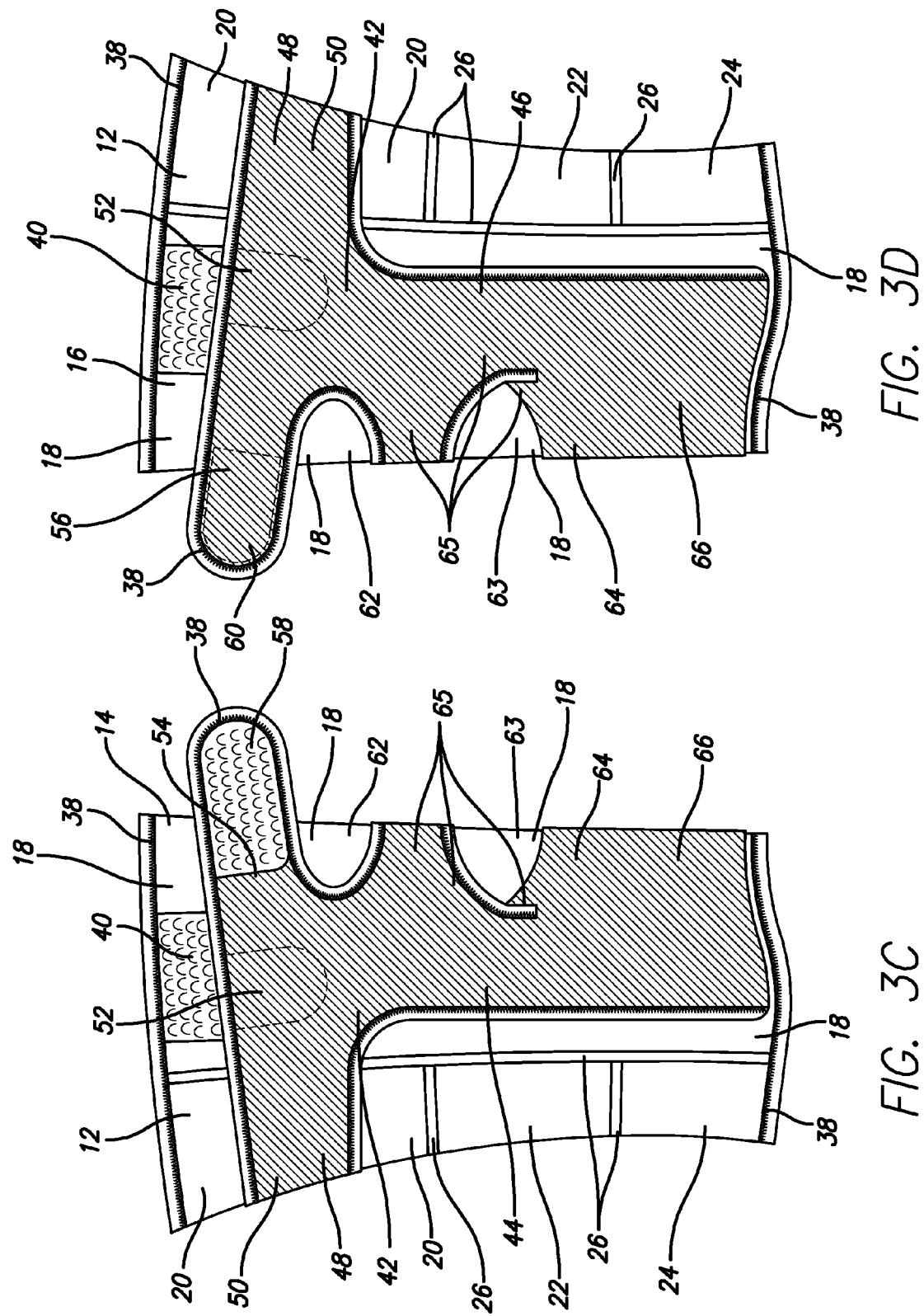

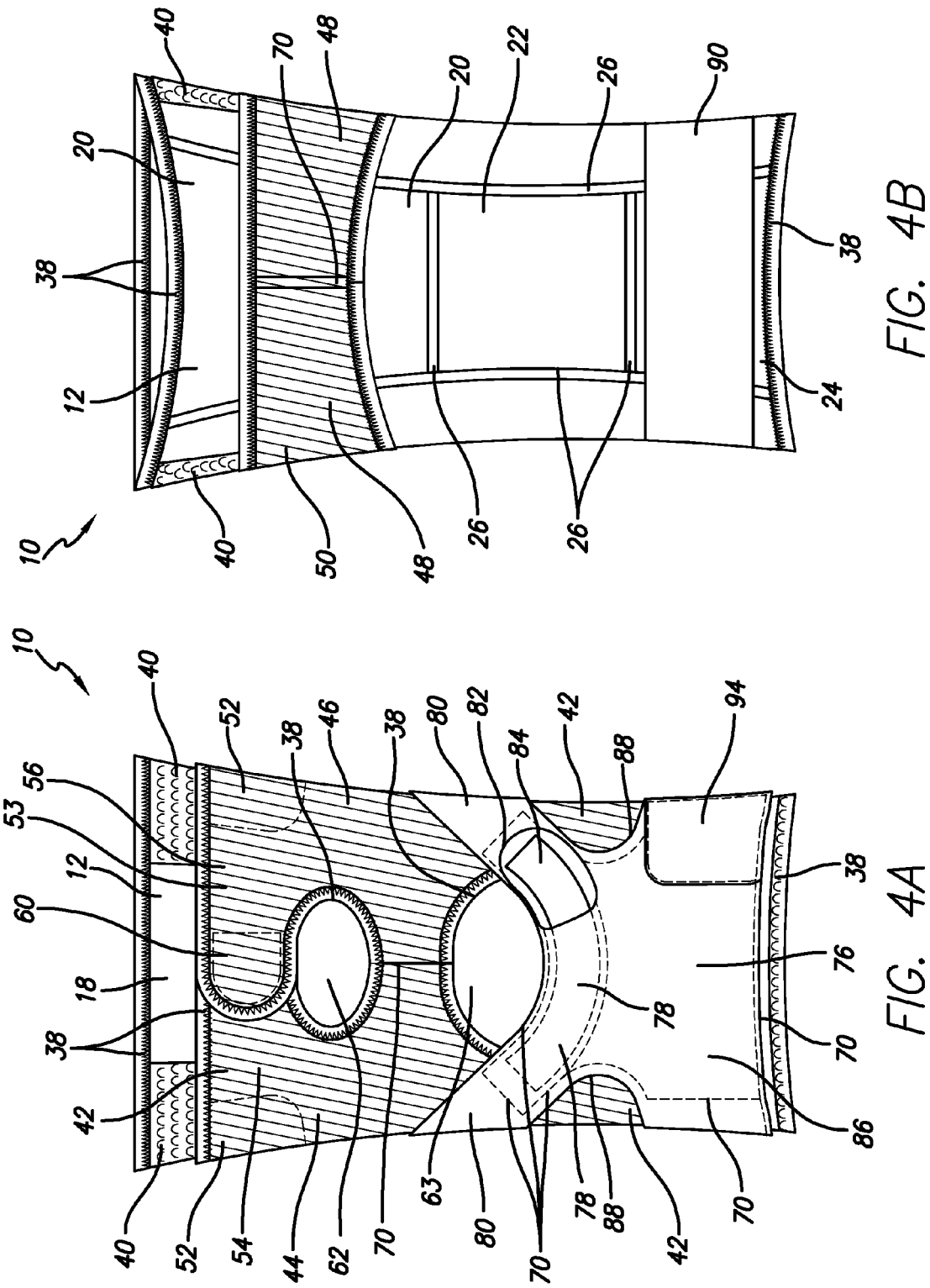

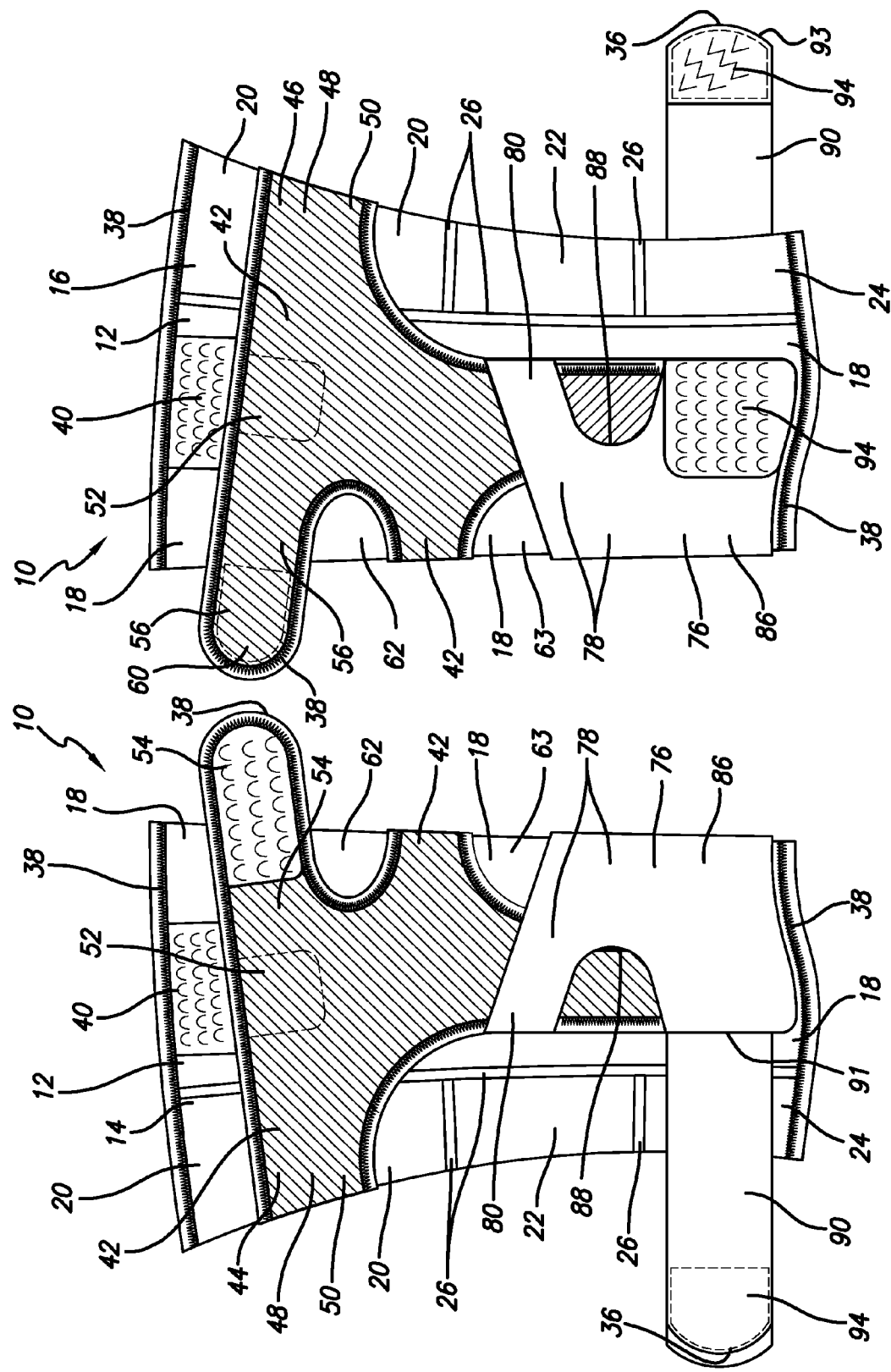

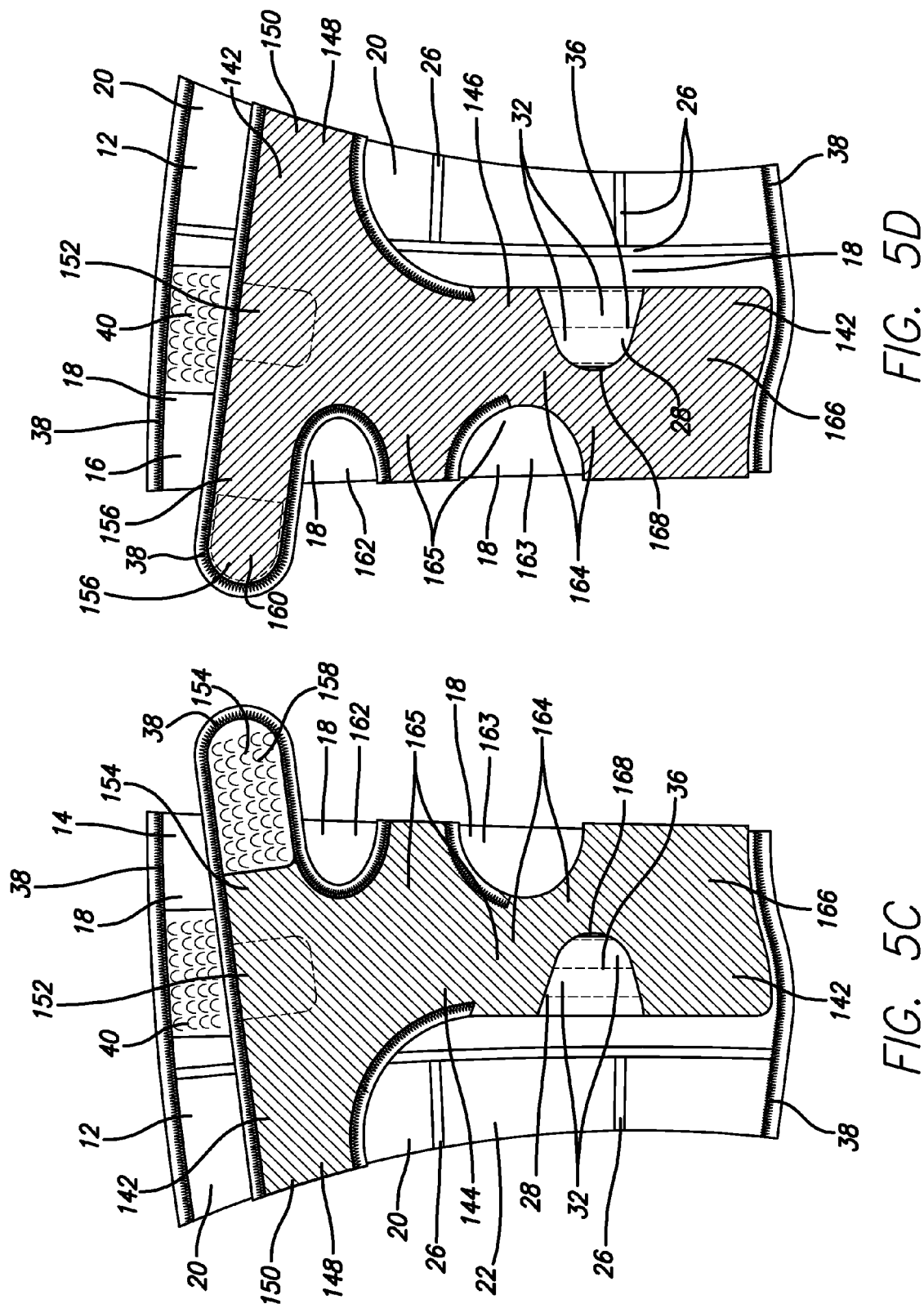

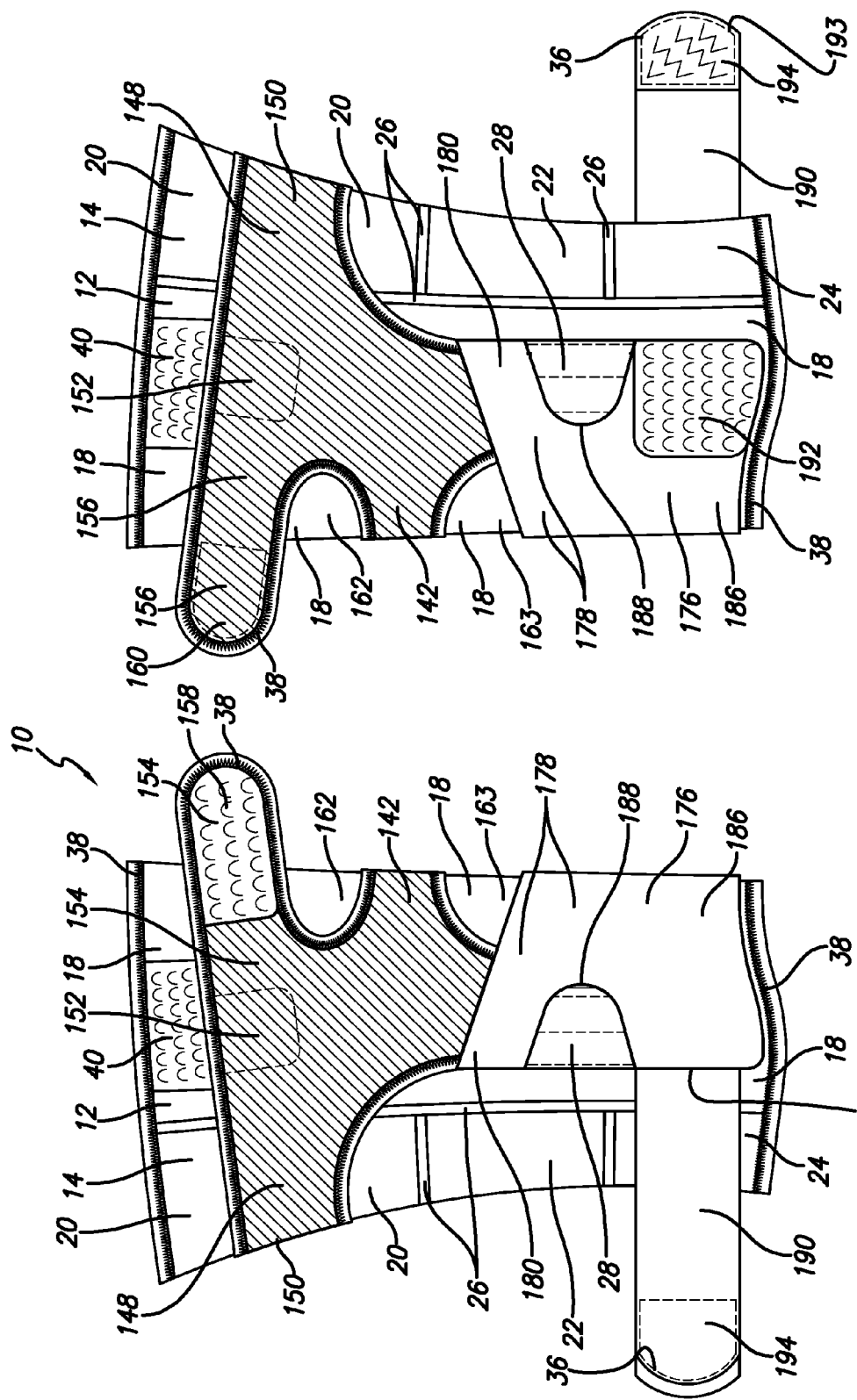

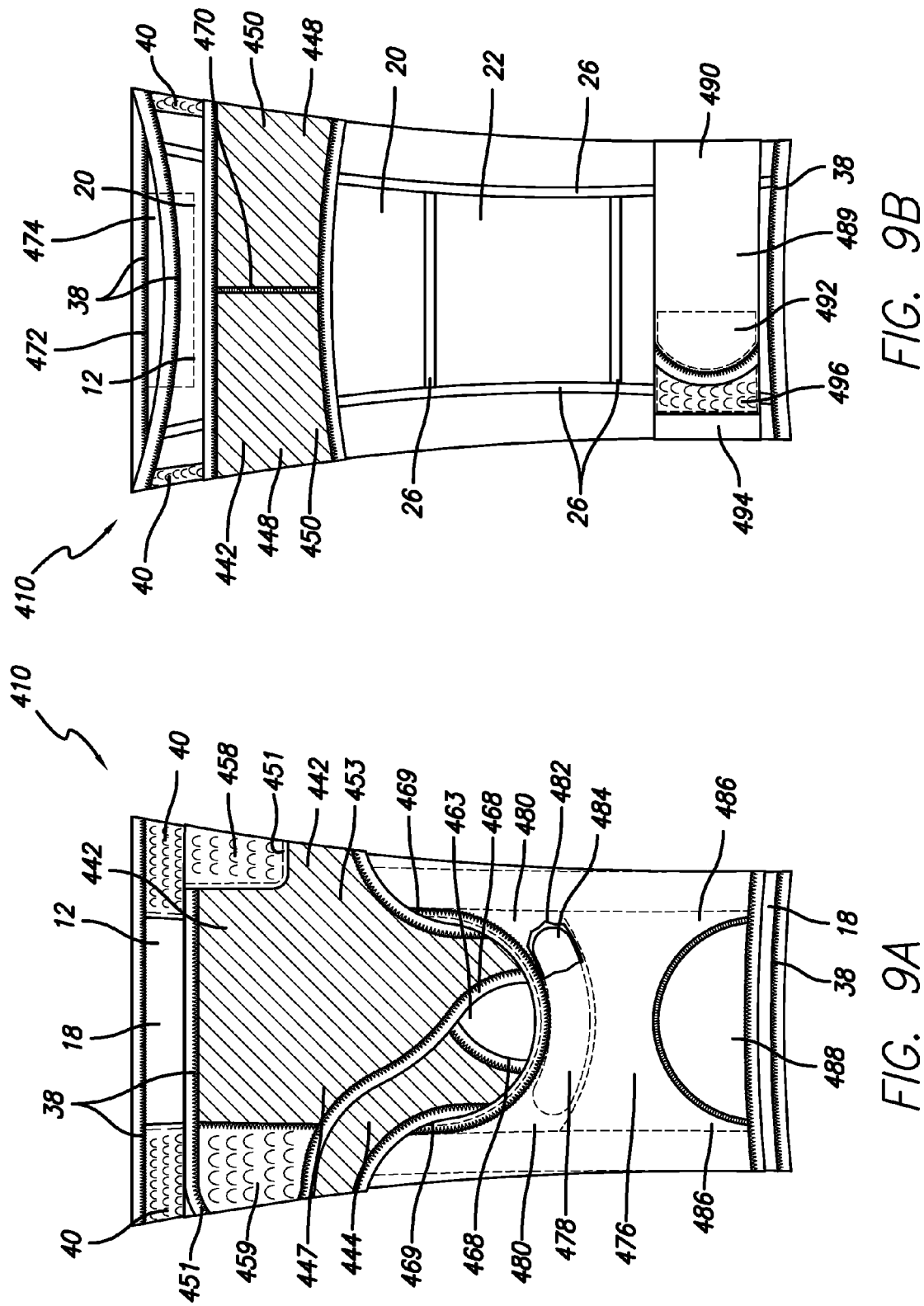

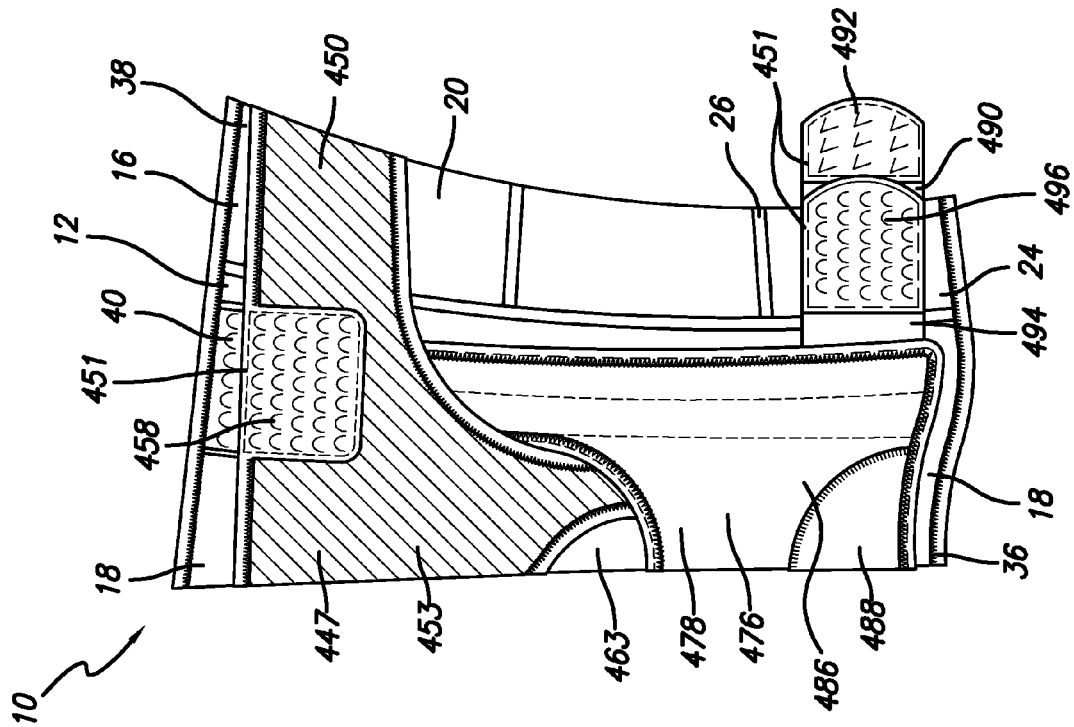
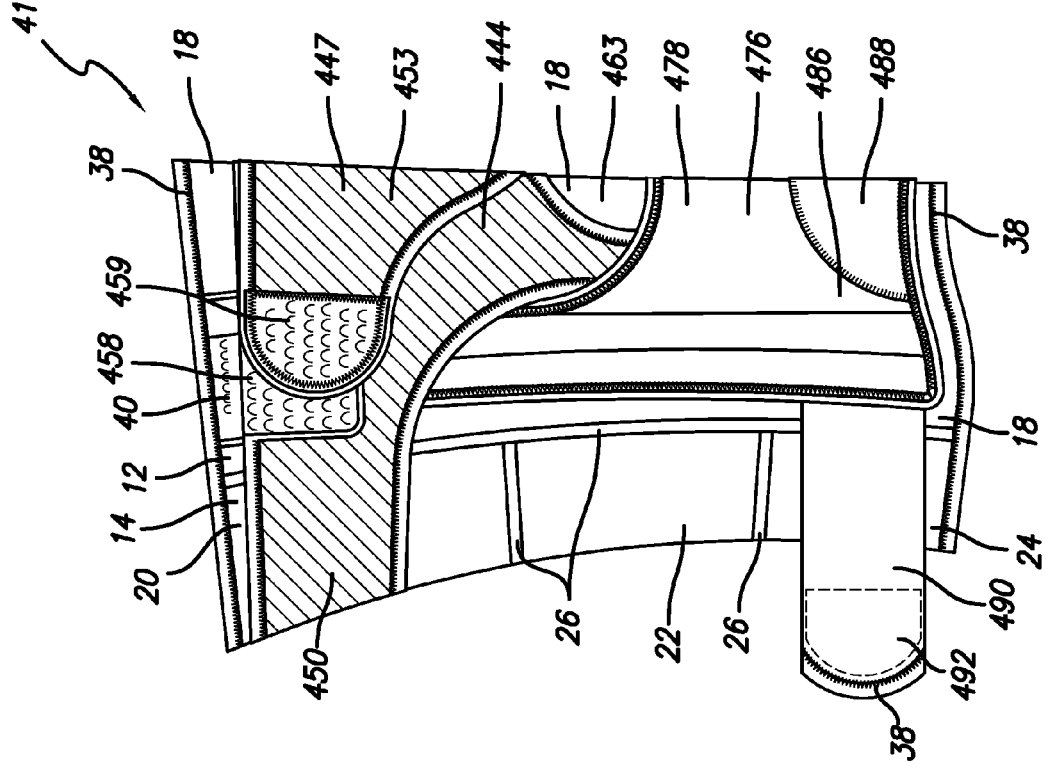

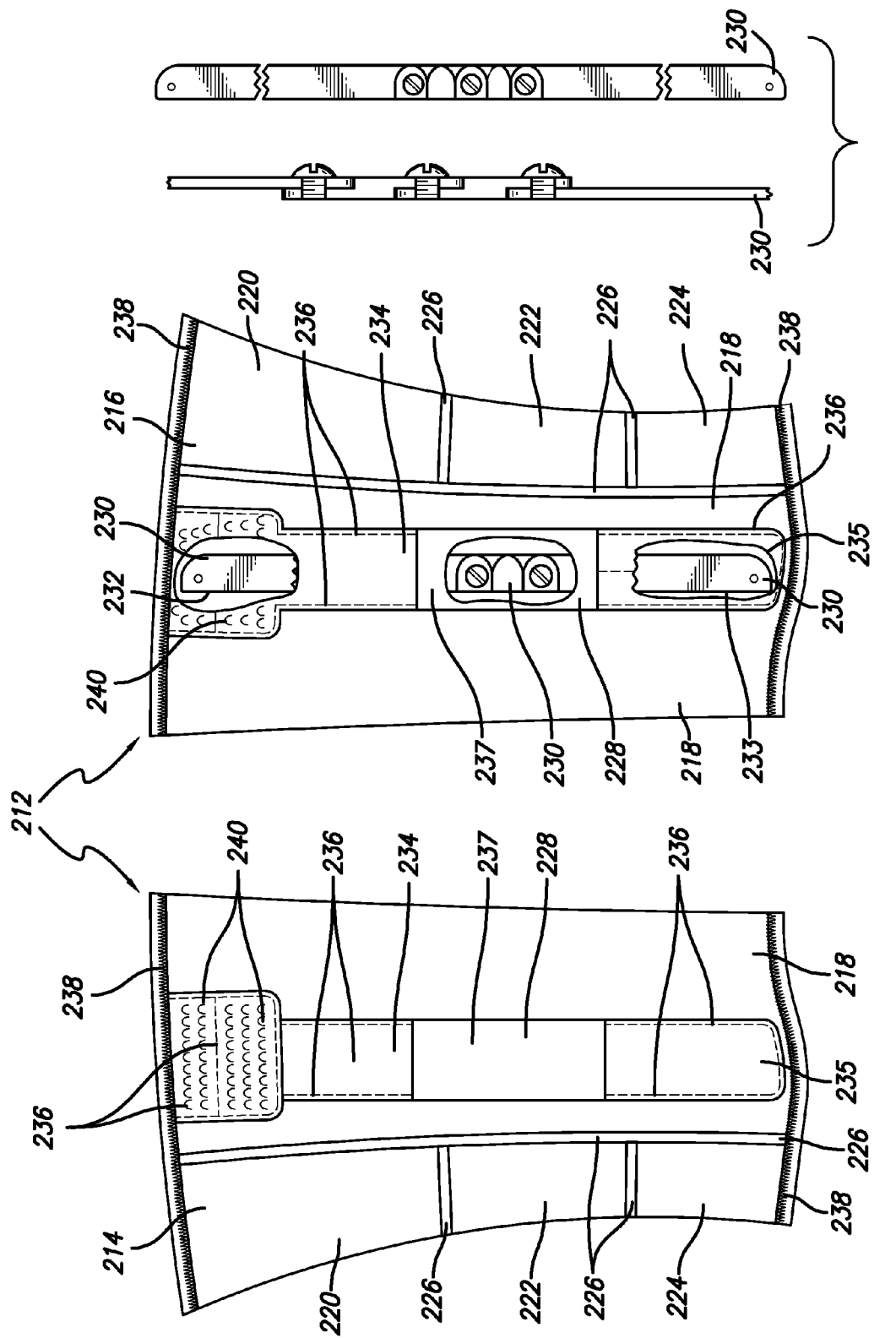

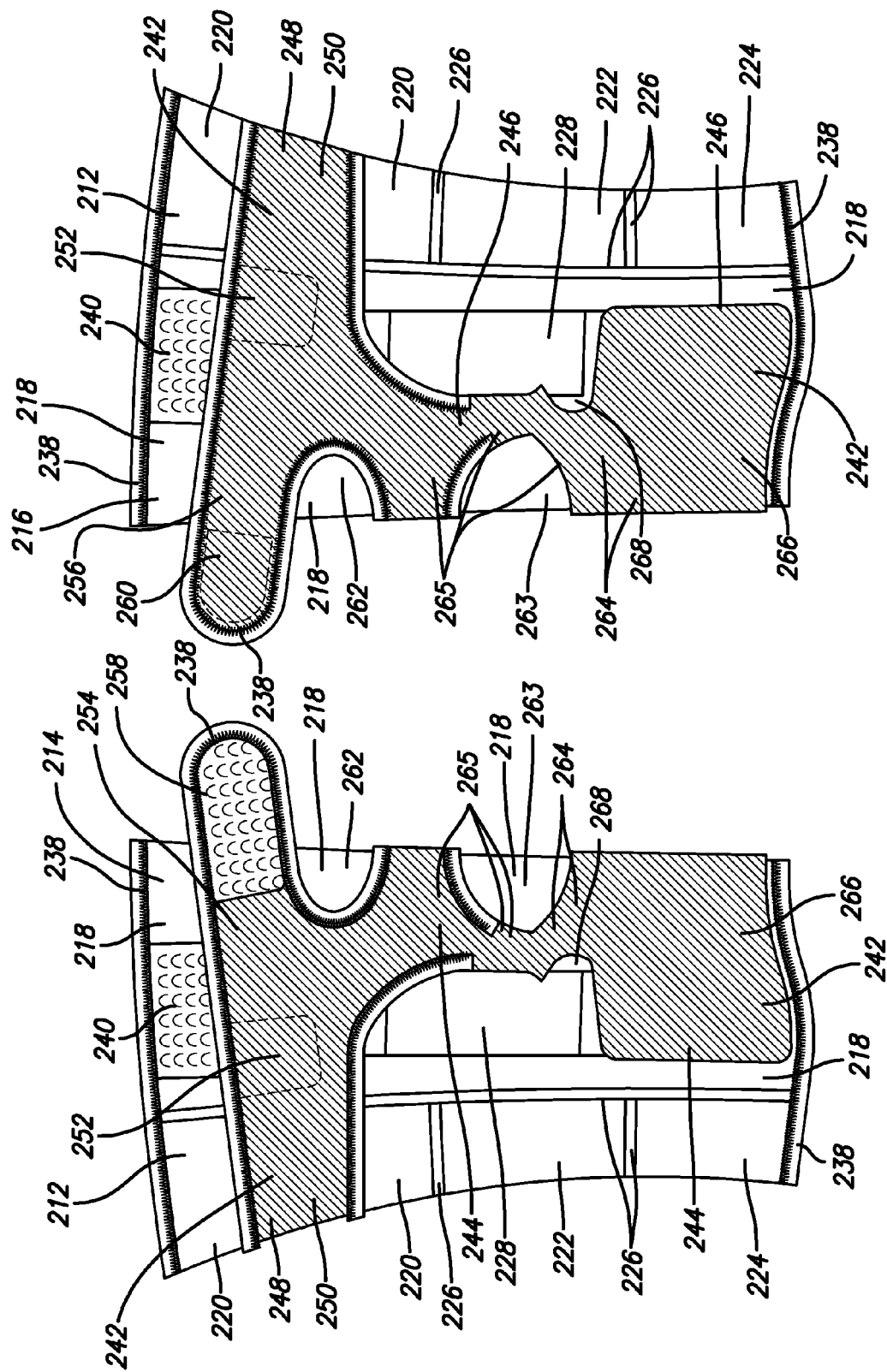

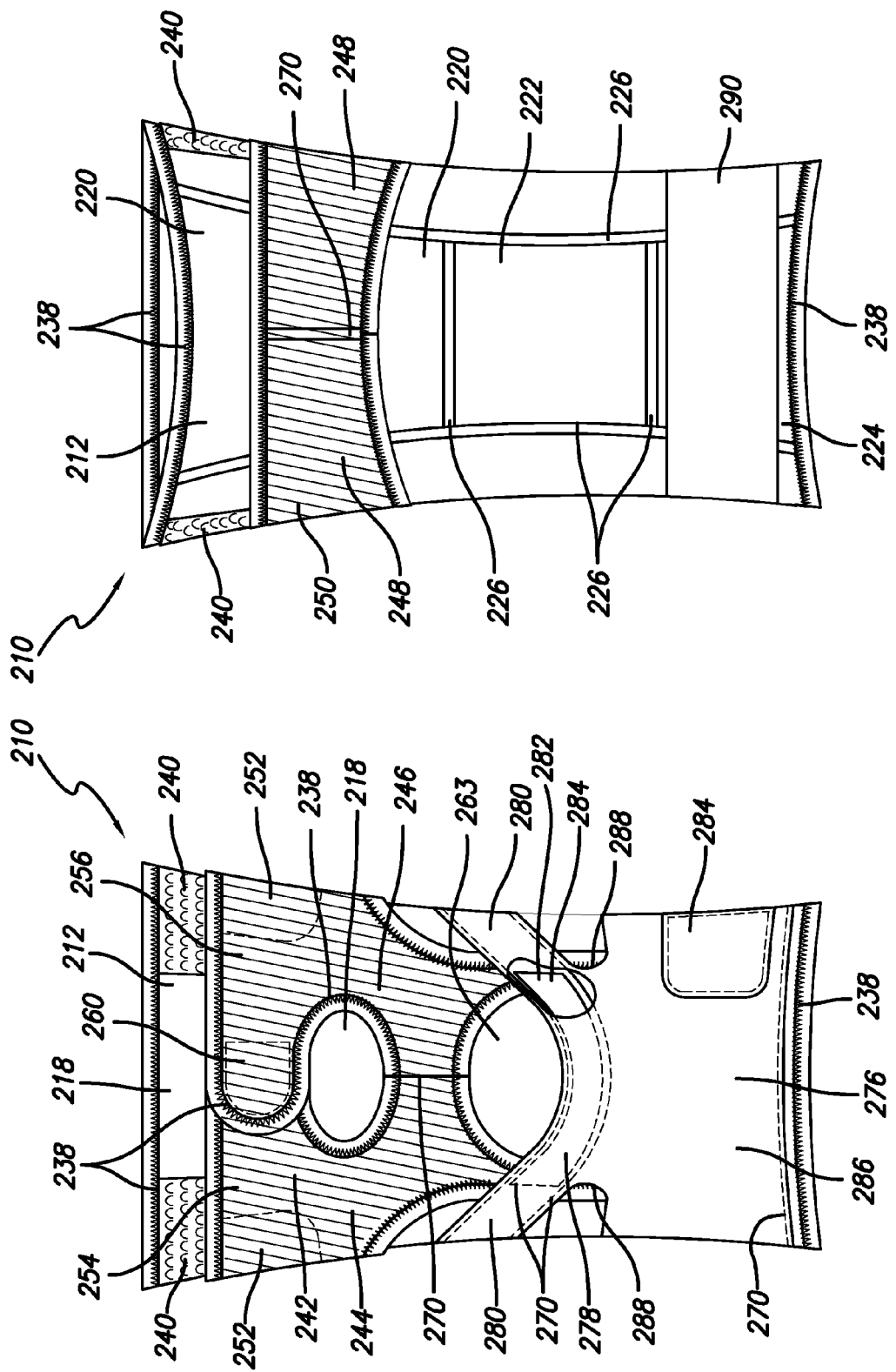

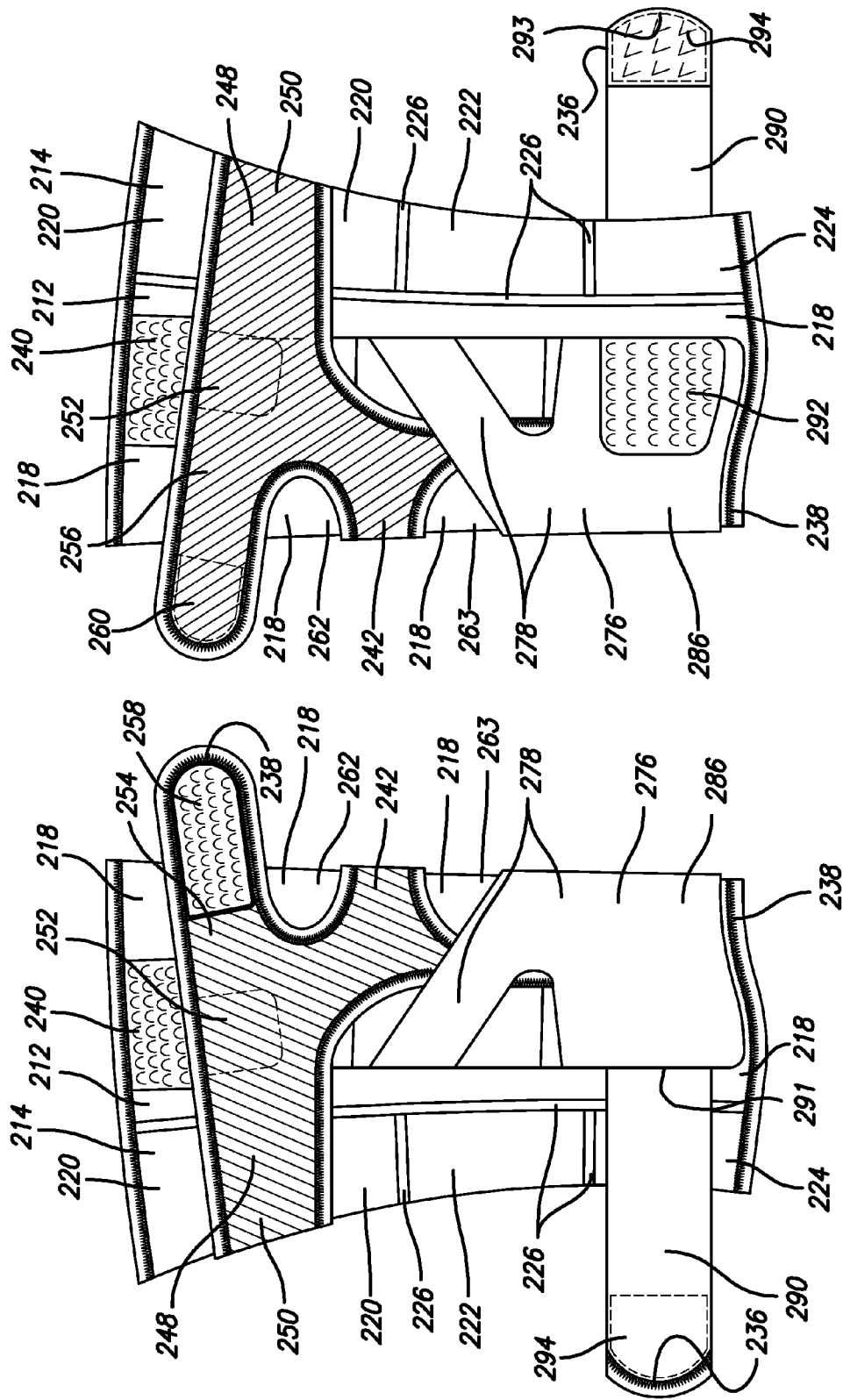

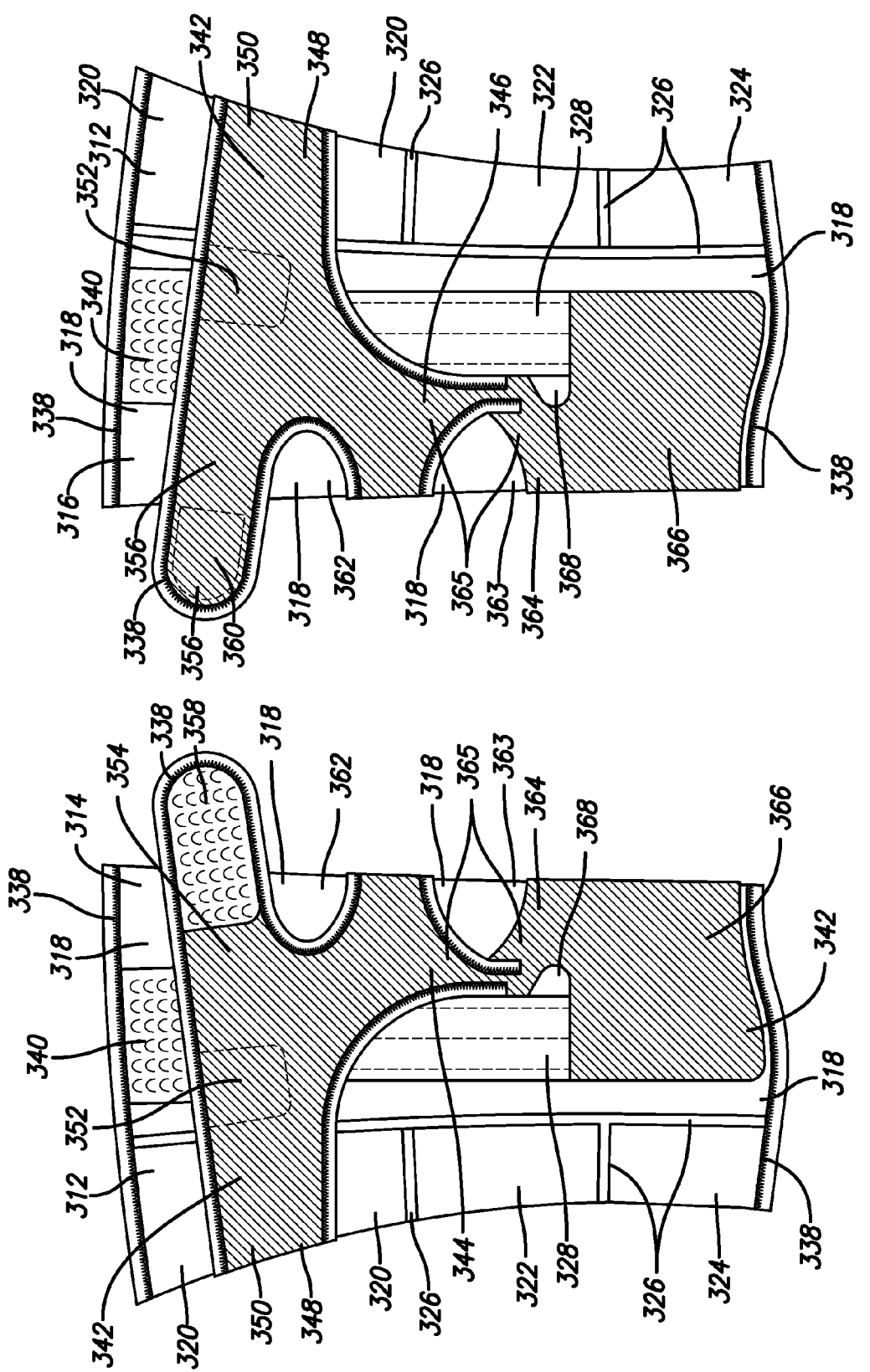

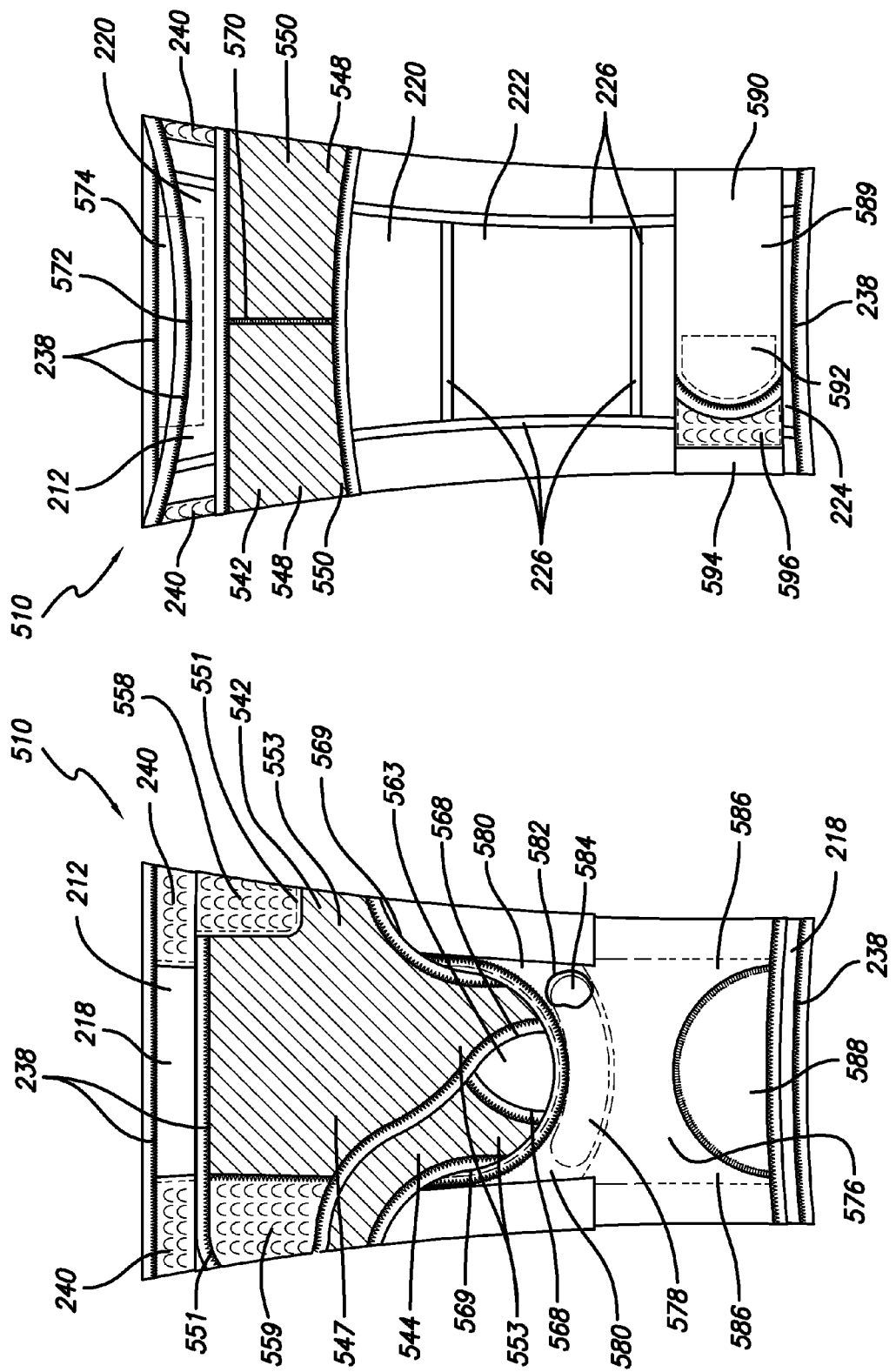

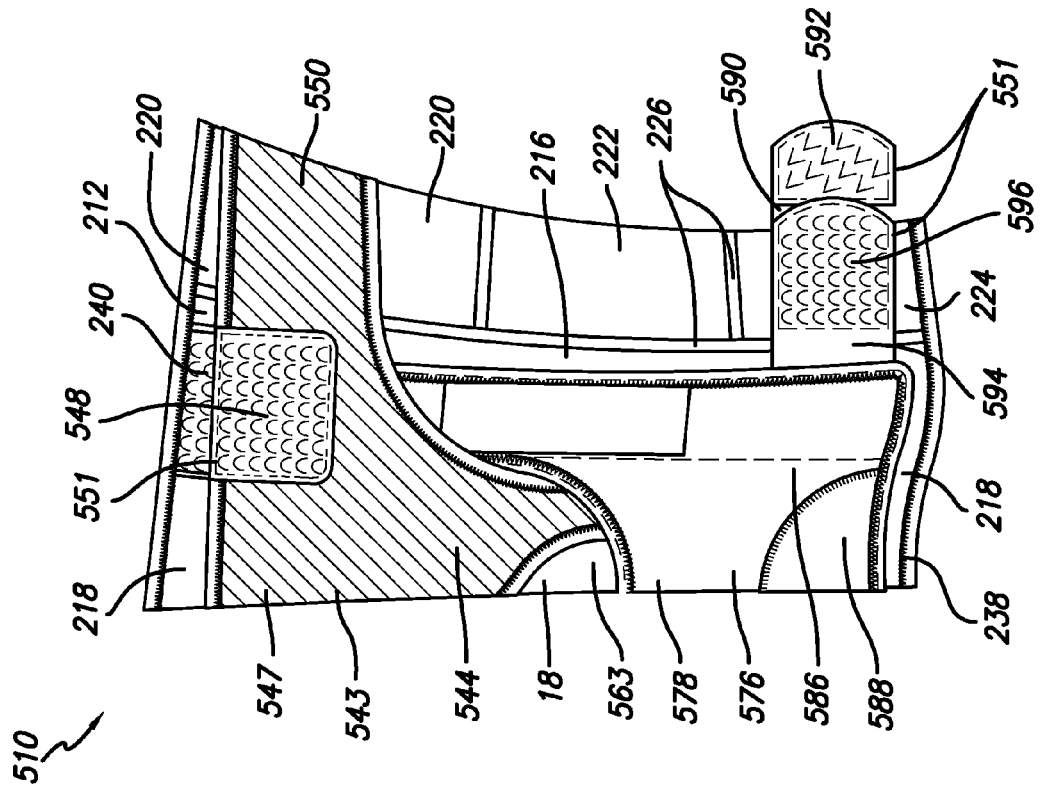
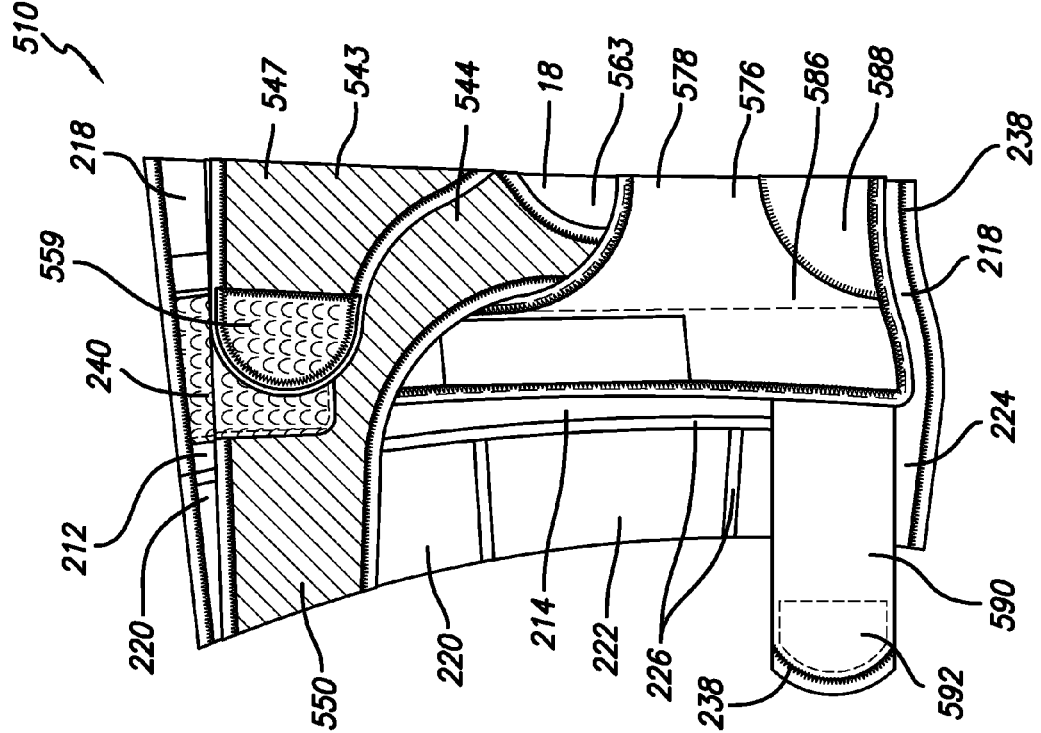
FIG. 19D
FIG. 19C

KNEE BRACE

CROSS-REFERENCE TO RELATED APPLICATIONS

This application claims priority to provisional application No. 60/733,374, filed Nov. 4, 2005, the disclosure of which is incorporated by reference. This application claims priority to provisional application No. 60/763,190, filed Jan. 28, 2006, the disclosure of which is incorporated by reference.

FIELD OF THE INVENTION

This invention relates generally to the field of articles worn by persons to reduce the likelihood, severity, or exacerbation of injury to the body, and more specifically to the field of braces worn on the knee.

BACKGROUND OF THE INVENTION

Flexible knee braces are used by athletes and other persons engaged in vigorous physical activity to protect the knee from injury and to avoid exacerbation of existing injury. The knee is one of the most heavily used joints of the body, as it is used in any activity that involves walking or running.

The knee is also a common subject of injury, due to the relatively high levels of stress it must bear under dynamic loads that are often multiples of the entire weight of the body. During normal ambulation, in occupations involving physical labor, and especially during strenuous sports, the knee can undergo abnormal motions as a result of quick changes in direction, fatigue, uneven surfaces, or impacts. These abnormal motions can cause sprains or more serious injuries, such as dislocation, stretching, or tearing of the tissues that make up the knee.

For these reasons, devices to protect the knee against abnormal motions have been used for many years, in a variety of specific embodiments which vary in their abilities to protect against different types of abnormal motions. One such prior art knee brace, called the PSB Knee Brace, is marketed by NEA International, BV of Maastricht, the Netherlands. The industrial design of the PSB Knee Brace is disclosed in FIGS. 3.1-3.6 in International Design DM/052483.

Many of the features of the PSB Knee Brace are known in the field of athletic braces. The PSB includes an elastic sleeve base with upright support members formed of resilient stay members placed in pockets located on each side of the base. The PSB Knee Brace also includes an aperture through which the patella (kneecap) extends when the brace is worn, and a patella support panel mounted at the position of the patellar tendon and below the patella when the brace is worn.

The PSB Knee Brace includes an elastic mesh support layer, on top of the elastic sleeve base. The elastic mesh support layer is positioned vertically above the patella and patella support panel when the brace is worn, and extends approximately to the vertical midpoint of the patella on each side of the patella. The elastic mesh support layer extends only slightly beyond the upper edge of the patella support panel when the brace is worn, where it is attached on each side by a single sewn seam approximately 2.5" long between the upper edge of the patella support panel and the elastic sleeve base. The elastic mesh support layer of the PSB Knee Brace does not extend below the patella, nor does it completely encircle the patella.

What is needed is a knee brace having an elastic sleeve base, upright support members, a patella support panel, and an elastic mesh support layer, wherein the construction of the brace is adapted to promote the cooperation between the elastic sleeve base, the patella support panel, and the elastic mesh support layer. What is further needed is a knee brace having an elastic sleeve base, upright support members, a patella support panel, and an elastic mesh support layer, wherein the construction of the brace is adapted to promote the cooperation between the elastic sleeve base, the patella support panel, and the elastic mesh support layer, and wherein the upright support member includes at least one mechanical hinge. What is further needed is a knee brace having an elastic sleeve base, upright support members, a patella support panel, and an elastic mesh support layer, wherein the elastic mesh support layer includes two side-by-side portions that are fastened together in at least a partially overlapping fashion.

SUMMARY OF THE INVENTION

A preferred embodiment of a knee brace according to the present invention includes an elastic base that covers the knee and adjacent portions of the upper leg and the lower leg of a person, a mesh support layer covering an upper portion of the base and extending below the knee when the brace is worn; and a below-knee support panel made of an inelastic sheet material.

A different embodiment of a knee brace according to the present invention includes an elastic base that covers the knee and adjacent portions of the upper leg and the lower leg of a person, a mesh support layer having a symmetric upper closure assembly that includes overlapping ears and extending below the knee when the brace is worn; and a below-knee support panel made of an inelastic sheet material.

An alternative embodiment of a knee brace according to the invention includes an elastic base that covers the patella tendon and portions of the upper leg and the lower leg of a person, a mesh support layer covering an upper portion of the base and including a patella strap portion that extends over at least the patella tendon when the brace is worn; and a below-knee support panel made of an inelastic sheet material.

Another embodiment of a knee brace according to the invention includes an elastic base that covers the area surrounding the kneecap and portions of the upper leg and the lower leg of a person, a mesh support layer covering an upper portion of the base and including a patella support portion covering the area surrounding the kneecap and encircling the kneecap when the brace is worn; and a below-knee support panel made of an inelastic sheet material.

A knee brace according to the invention may include one or more upright support members located on a side portion of the base. The upright support member can include, for example, a resilient stay in an elongated pocket fixed to a side of the base, or a mechanical hinge having ends that fit into upper and lower pockets fixed to a side of the base.

In a knee brace according to the invention, the mesh support layer can include a lower portion sewn between the below-knee support panel and the base. However, this is not required, and the mesh support layer could be sewn on top of the below-knee support panel so that the below-knee support panel is sewn between the mesh support layer and the base.

In a knee brace according to the invention, the upper portion of the mesh support layer can include an above-knee rear strap and an above-knee front strap comprising a first strap portion and a second strap portion that can be releasably fastened together, for example using hook and loop material of the type sold under the trademark VELCRO, to tighten the above-knee front strap about the upper leg of the wearer.

In a knee brace according to the invention, the upper portion of the mesh support layer can include at least one suspension tab, and the base can include at least one suspension patch, whereby the suspension tab of the upper portion of the mesh support layer can be releasably fastened to the suspension patch of the base to position the upper portion of the mesh support layer on the base.

A knee brace according to the invention can include a below-knee strap closure assembly that can be releasably fastened around the lower leg, for example using one or more elastic straps and hook and loop material of the type sold under the trademark VELCRO, to tighten the below-knee strap about the lower leg of the wearer.

Further objects, features, and advantages of the invention will be apparent from the following detailed description when taken in conjunction with the accompanying drawings.

BRIEF DESCRIPTION OF THE DRAWINGS

In the drawings:

FIGS. 1(a) and 1(b) present right side and left side views, respectively, of an exemplary base with resilient stay members for use in a preferred embodiment of a knee brace according to the invention;

FIG. 2 presents front and side views of an exemplary resilient stay member for use in the base of FIGS. 1(a)-1(b);

FIGS. 3(a)-3(d) present front, rear, right side, and left side views, respectively, of an exemplary mesh support layer for use in a preferred embodiment of a knee brace according to the invention;

FIGS. 4(a)-4(d) present front, rear, right side, and left side views, respectively, of a preferred embodiment of a knee brace according to the invention that includes the mesh support layer of FIGS. 3(a)-3(d);

FIGS. 5(a)-5(d) present front, rear, right side, and left side views, respectively, of an alternative mesh support layer for use in an alternative knee brace according to the invention;

FIGS. 6(a)-6(d) present front, rear, right side, and left side views, respectively, of an alternative knee brace according to the invention that includes the mesh support layer of FIGS. 5(a)-5(d);

FIGS. 9(a)-9(d) present front, rear, right side, and left side views, respectively, of a preferred embodiment of a knee brace according to the invention that includes the mesh support layer of FIGS. 7(a)-7(b) and the base of FIGS. 1(a)-1(b);

FIGS. 10(a) and 10(b) present an alternative base with mechanical hinges for use in an alternative embodiment of a knee brace according to the invention;

FIG. 11 presents front and side views of an exemplary mechanical hinge for use in a knee brace according to the invention;

FIGS. 12(a)-12(d) present front, rear, right side, and left side views, respectively, of an exemplary mesh support layer for use in an alternative knee brace with mechanical hinges according to the invention;

FIGS. 13(a)-13(d) present front, rear, right side, and left side views, respectively, of an alternative knee brace according to the invention that includes the mesh support layer of FIGS. 12(a)-i 2(d) and the base of FIGS. 10(a)-10(b), with the mechanical hinges and hinge cover removed;

FIGS. 16(a)-16(d) present front, rear, right side, and left side views, respectively, of another alternative mesh support layer for use in a knee brace according to the invention;

FIGS. 19(a)-19(d) present front, rear, right side, and left side views, respectively, of an alternative knee brace according to the invention that includes the mesh support layer of FIGS. 17(a)-17(b) and the base of FIGS. 10(a)-10(b).

DETAILED DESCRIPTION OF THE INVENTION

Figure 5B:
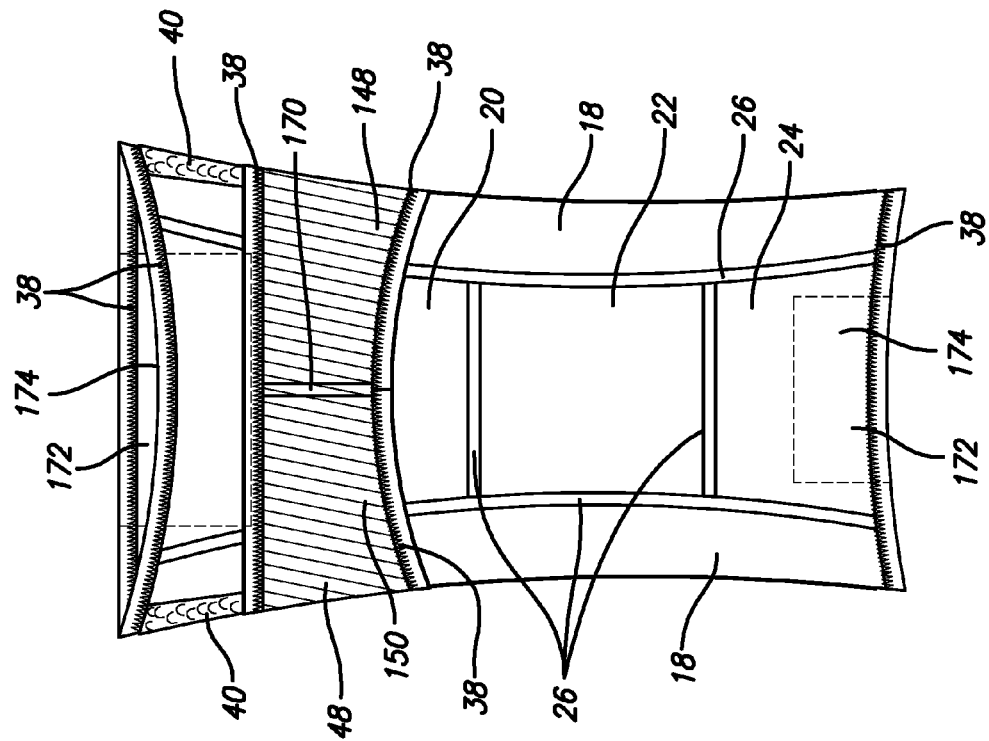

Referring to the drawings:

FIGS. 1(a) and 1(b) present right side and left side views, respectively, of an exemplary base 12 with resilient stay members for use in a preferred embodiment of a knee brace according to the invention. FIG. 1(a) shows the first (right) side 14 of the base 12, while FIG. 1(b) shows the second (left) side 16 of the base 12. The construction of the exemplary base 12 is for illustration only, and other constructions could be used in a knee brace according to the invention.

The base 12 preferably includes a front panel 18 and is made of, for example, an elastic sheet material such as polyester, spandex, or neoprene or other similar material suitable for use in an athletic brace. The rear of the base 12 is preferably, but not necessarily, formed of three panels, a rear upper panel 20, a rear central panel 22, and a rear lower panel 24. The front panel 18, rear upper panel 20, rear central panel 22, and rear lower panel 24 are preferably, but not necessarily, joined together using stitched seams 26. The base 12 may include edge binding 38 to finish any exposed edges, such as the cuffs of the base 12, although this is not required.

The base 12 preferably includes one or more upright support members 28 located on one or both sides of the base 12. Each upright support member can be formed, for example, by placing a resilient stay 30 in an upright support pocket 32 formed using a side pocket cover strip 34 mounted to the side of the base 12 using stitches 36.

The base 12 also includes an upper mesh support suspension fastening patch 40 mounted to the upper side portion of the base 12. The upper mesh support fastening patch 40 is preferably a loop-type material of the type marketed under the trademark VELCRO.

FIG. 2 presents front and side views of an exemplary resilient stay member 30 for use in a preferred embodiment of a knee brace according to the invention. The resilient stay member 30 can be formed, for example, of a flattened spiral core of stainless steel or other flexible material. Other resilient stay constructions known in the art can be used, such as bunched or individual resilient rods or fibers, narrow strips of reinforcing sheet material, or combinations or equivalents of these various alternatives. Other materials can also be used, such as such as fiberglass, graphite, plastic, or metal.

FIGS. 3(a)-3(d) present front, rear, right side, and left side views, respectively, of an exemplary mesh support layer, indicated generally at 42, for use in a preferred embodiment of a knee brace according to the invention. The mesh support layer 42 is preferably made of an elastic sheet material that is strong yet porous and lightweight, such as a polyester or nylon material. The mesh support later 42 is preferably formed using a first (right) mesh support panel 44 and a second (left) mesh support panel 46 which are joined together, for example, by stitched seams 70.

The mesh support layer 42 preferably includes an above-knee rear mesh strap 50 at the back of the thigh. The above-knee rear mesh strap 50 can be formed, for example, by including an above-knee rear mesh strap portion 48 on each of the first mesh support panel 44 and the second mesh support panel 46, and joining the two above-knee rear mesh strap portions 48 at the back of the thigh using stitched seams 70.

The mesh support panel 42 preferably also includes a mesh support layer suspension fastening tab 52 which is preferably formed of hook-type material of the type marketed under the trademark VELCRO.

The mesh support layer 42 preferably also includes an above-knee front strap 53 at the front of the thigh. The above-knee front strap 53 can be formed, for example, using a right front strap portion 54 formed as part of the first mesh support panel 44 and a left front strap portion 56 formed as part of the second mesh support panel 46.

The right front strap portion 54 preferably includes a fastening patch 58 formed of loop-type material of the type marketed under the trademark VELCRO. The left front strap portion 56 preferably includes a fastening tab 60 which is preferably formed of hoop-type material of the type marketed under the trademark VELCRO. The right front strap portion 54 is detachably attachable to the left front strap portion 56 by pressing the fastening tab 60 against the fastening patch 58, to secure the above-knee front strap 53 around the thigh of the wearer of the brace.

The mesh support layer 42 preferably includes an above-knee aperture 62 between the above-knee front strap 53 and the lower portion of the brace.

The mesh support 42 can include a patella strap mesh portion 64 as shown, for example, in FIG. 3(*a*) extending underneath the patella strap portion 78 of the below-knee support panel 76 as shown, for example, in FIG. 4(*a*). The mesh support 42 can include a patella support mesh portion 65 as shown, for example, in FIG. 3(*a*) encircling the kneecap when the brace is worn. The mesh support 42 can include a below-knee mesh portion 66 as shown, for example, in FIG. 3(*a*) positioned vertically below the area of the kneecap when the brace is worn.

The mesh support layer 142 is preferably attached to the sides of the base 12 using stitched seams 170.

The base 12 preferably includes one or more cuff reinforcements 72 at the upper and/or lower cuffs of the base. One or more non-slip patches 74 may also be provided on the inside of the upper and/or lower cuffs of the base to inhibit movement of the base on the leg during use.

FIGS. 4(*a*)-4(*d*) present front, rear, right side, and left side views, respectively, of a preferred embodiment of a knee brace according to the invention that includes the mesh support layer of FIGS. 3(*a*)-3(*d*). The completed brace of FIGS. 4(*a*)-4(*d*) adds a below-knee support panel, indicated generally at 76, and a below-knee elastic strap, indicated generally at 90, to the base and mesh support layer of FIGS. 3(*a*)-3(*d*).

The below-knee support panel 76 is preferably formed, for example, of a durable inelastic sheet material such as leather, sheet vinyl, synthetic suede, or the material sold under the trademark KEVLAR. The below-knee support panel 76 includes a patella strap panel portion 78, roughly semicircular in shape, and positioned above the patella tendon located vertically below the kneecap when the brace is worn on the leg of a person. The patella strap panel portion 78 extends from one support panel end 80 to another support panel end 80. The patella strap panel portion 78 covers a patella support member pocket 82 formed, for example, by stitched seams 70. A patella support member 84 can be placed in the patella support member pocket 82.

The below-knee support panel 76 also includes a below-knee strap panel portion 86. The support panel 76 may include cutouts 88 on each side of the panel 76, for example so that the support panel can flex more readily below the patella strap panel portion 78 as the knee bends.

The brace 10 may also include a below-knee elastic strap 90. The below-knee elastic strap 90 extends from a first end 91 to a second end 93. The first end 91 is preferably permanently fixed to the base 12, the support panel 76, and or the edge of the mesh support 42, for example by sewing. The second end 93 is preferably not permanently fixed to the base 12 or support panel 76. Instead, the second end 93 of the below-knee elastic strap 90 preferably includes a fastening tab 94 formed of hook-type material of the type sold under the trademark VELCRO for releasable attachment to a below-knee strap fastening patch 92 secured to the below-knee support panel 76, for example by stitched seams 36.

Figure 5A:
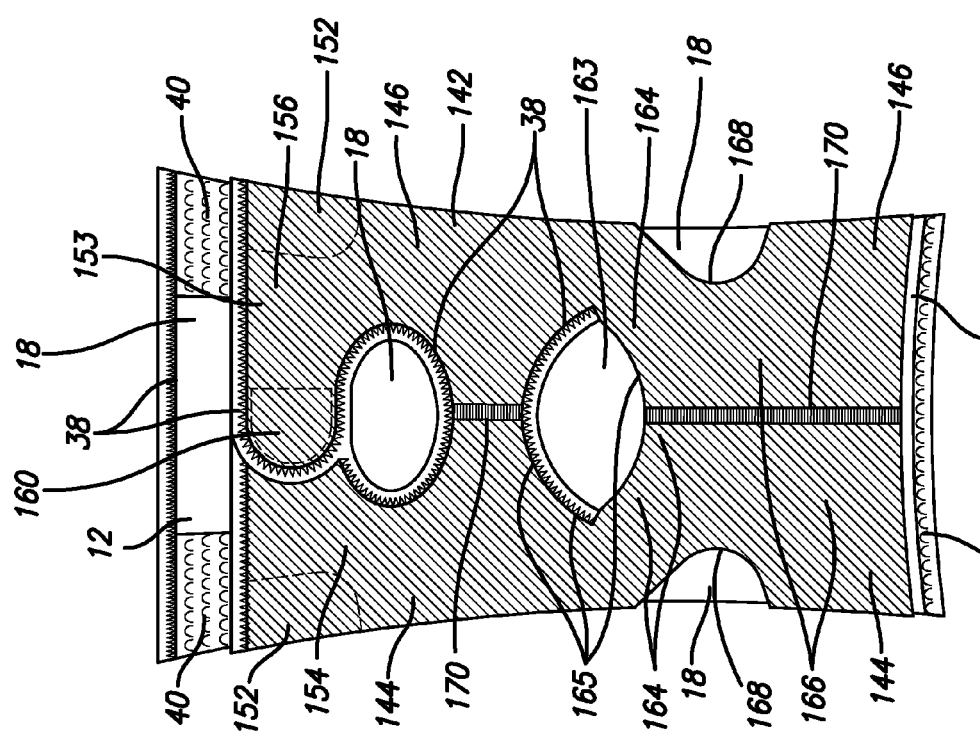

FIGS. 5(*a*)-5(*d*) present front, rear, right side, and left side views, respectively, of an alternative mesh support layer 142 for use in an alternative knee brace according to the invention. The mesh support layer 142 is preferably made of an elastic sheet material that is strong yet porous and lightweight, such as a polyester or nylon material. The alternative mesh support layer 142 is preferably formed using a first (right) mesh support panel 144 and a second (left) mesh support panel 146 that may be joined together, for example, by stitched seams 170.

The mesh support layer 142 preferably includes an above-knee rear mesh strap 150 at the back of the thigh. The above-knee rear mesh strap 150 can be formed, for example using an above-knee rear mesh strap portion 148 formed as part of each of the first support panel 144 and the second support panel 146.

The mesh support layer 142 preferably also includes a suspension fastening tab 152 formed of hook-type material of the type sold under the trademark VELCRO.

The mesh support layer 142 preferably also includes an above-knee front strap 153 which may be formed, for example, using a right front strap portion 154 and a left front strap portion 156. The right front strap portion 154 can be formed as part of the first support panel 144 and the left front strap portion 156 can be formed as part of the left support panel 146. The right front strap portion 154 preferably includes a fastening patch 158, preferably formed of loop-type material of the type sold under the trademark VELCRO. The left front strap portion 156 preferably includes a fastening tab 160 that may be formed of hook-type material of the type sold under the trademark VELCRO.

The mesh support layer 142 preferably includes an above-knee aperture 162 between the above-knee strap 153 and the kneecap.

Figure 6B:
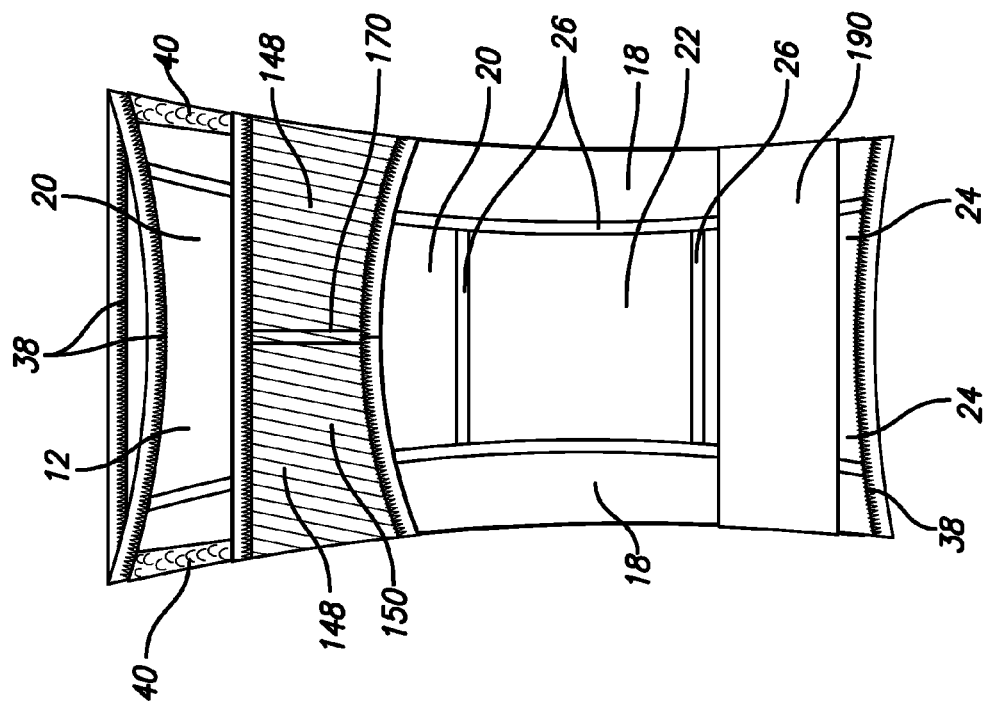
Figure 6A:
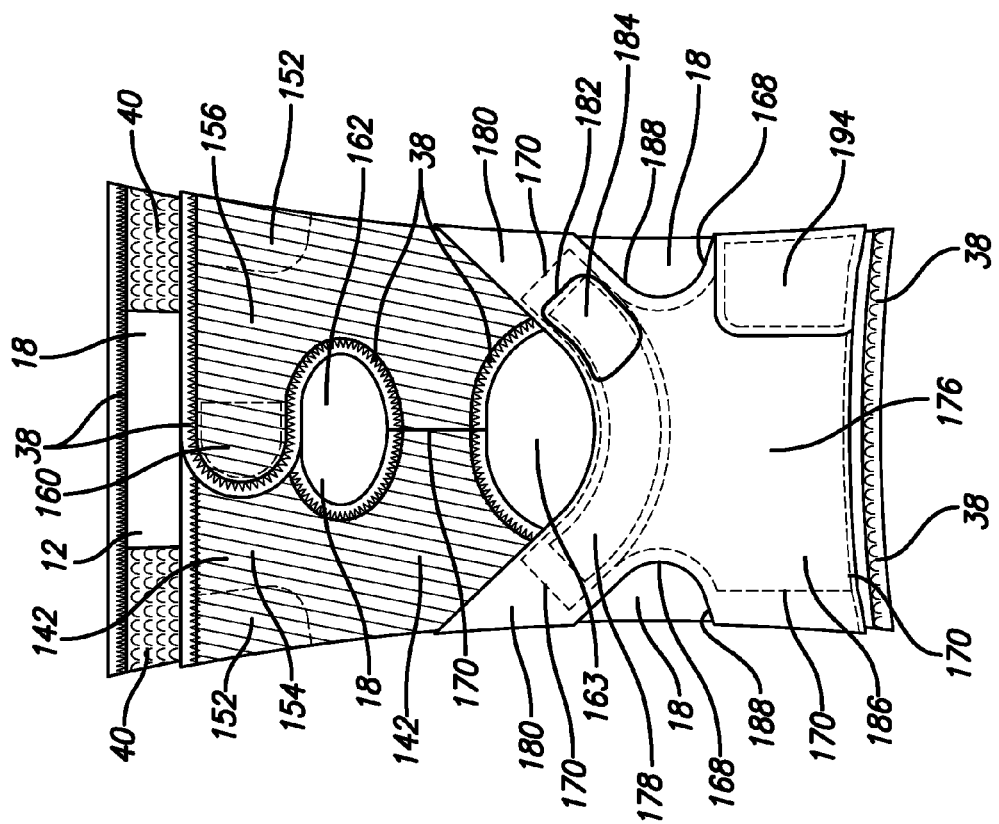

The mesh support 142 can include a patella strap mesh portion 164 as shown, for example, in FIG. 5(*a*) extending underneath the patella strap portion 178 of the below-knee support panel 176 as shown, for example, in FIG. 6(*a*). The mesh support 142 can include a patella support mesh portion 165 as shown, for example, in FIG. 5(*a*) encircling the kneecap when the brace is worn. The mesh support 142 can include a below-knee mesh portion 166 as shown, for example, in FIG. 5(*a*) positioned vertically below the area of the kneecap when the brace is worn.

The mesh support layer 142 can include side cutouts 168 on each side.

The mesh support layer 142 is preferably attached to the sides of the base 12 using stitched seams 170.

The base 12 preferably includes one or more cuff reinforcements 172 at the upper and/or lower cuffs of the base. One or more non-slip patches 174 may also be provided on the inside of the upper and/or lower cuffs of the base to inhibit movement of the base on the leg during use.

FIGS. 6(a)-6(d) present front, rear, right side, and left side views, respectively, of an alternative knee brace according to the invention, indicated generally at 110, that includes the mesh support layer 142 of FIGS. 5(a)-5(d). The completed brace of FIGS. 6(a)-6(d) adds a below-knee support panel 176 and a below-knee elastic strap 190 to the base 12 and mesh support layer 142 of FIGS. 5(a)-5(d).

The below-knee support panel 176 is preferably formed, for example, of a durable inelastic sheet material such as leather, sheet vinyl, synthetic suede, or the material sold under the trademark KEVLAR. The below-knee support panel 176 includes a patella strap panel portion 178, roughly semicircular in shape, and positioned above the patella tendon located vertically below the kneecap when the brace is worn on the leg of a person. The patella strap panel portion 178 extends from one support panel end 180 to another support panel end 180. The patella strap panel portion 178 covers a patella support member pocket 182 formed, for example, by stitched seams 170. A patella support member 184 can be placed in the patella support member pocket 182.

The below-knee support panel 176 also includes a below-knee strap panel portion 186. The support panel 176 may include cutouts 188 on each side of the panel 176, for example so that the support panel can flex more readily below the patella strap panel portion 178 as the knee bends.

The brace 110 may also include a below-knee elastic strap 190. The below-knee elastic strap 190 extends from a first end 191 to a second end 193. The first end 191 is preferably permanently fixed to the base 12, the support panel 176, and or the edge of the mesh support 142, for example by sewing. The second end 193 is preferably not permanently fixed to the base 12 or support panel 176. Instead, the second end 193 of the below-knee elastic strap 190 preferably includes a fastening tab 194 formed of hook-type material of the type sold under the trademark VELCRO for releasable attachment to a below-knee strap fastening patch 192 secured to the below-knee support panel 176, for example by stitched seams 36.

Figure 7A:
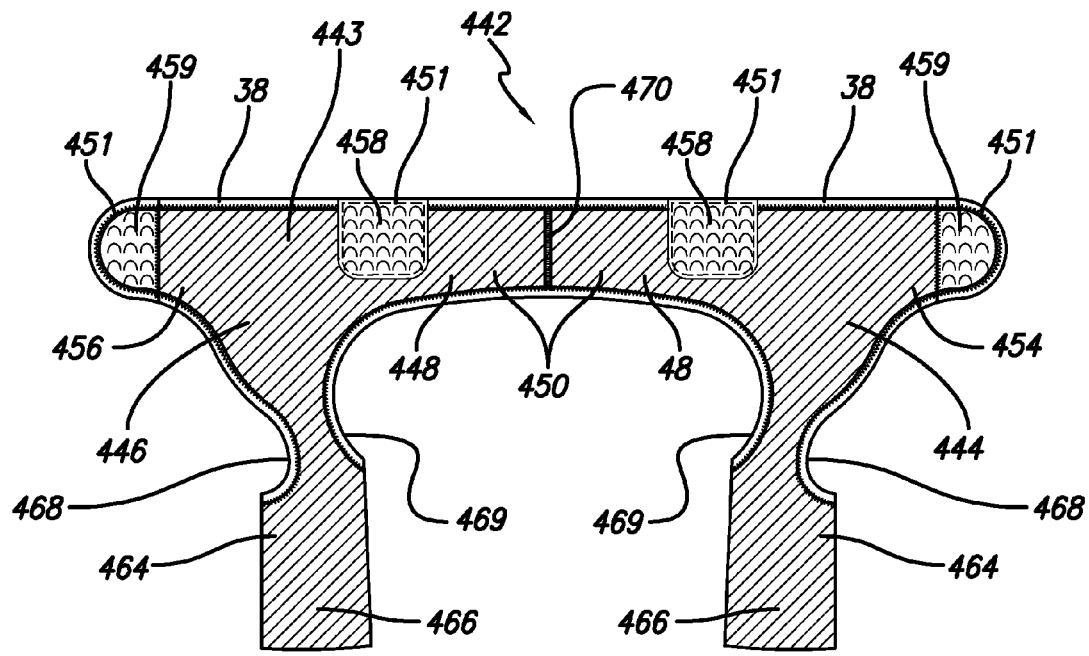
FIGS. 7(a)-7(b) present front and rear views, respectively, of an exemplary mesh support layer for use in a preferred embodiment of a knee brace according to the invention.
Figure 7B:
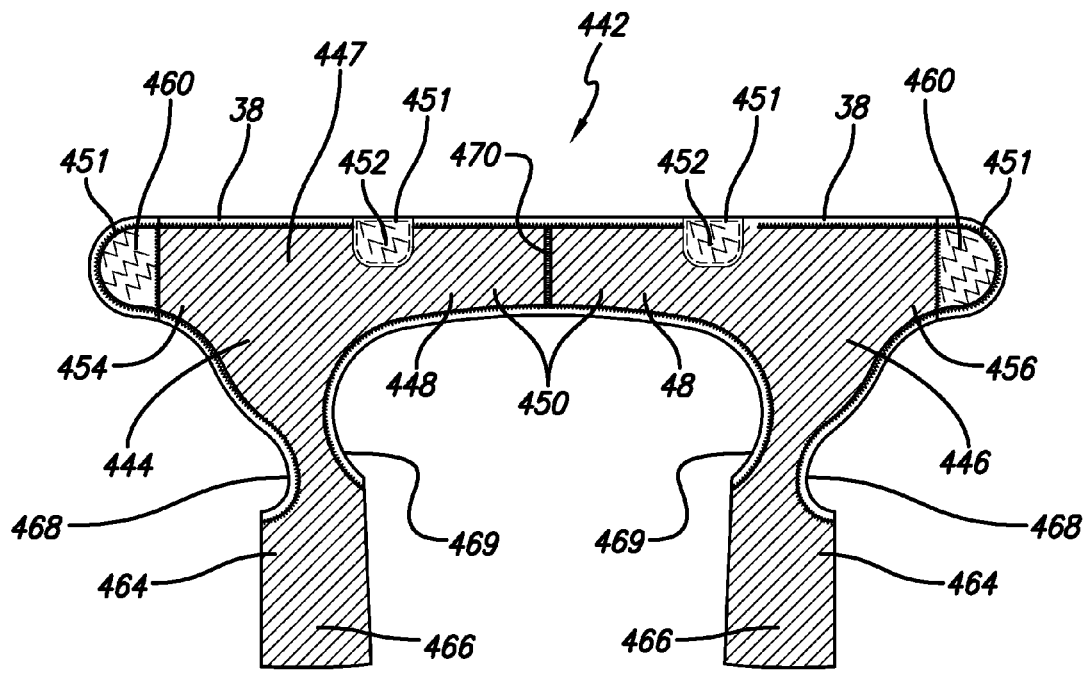
Figure 8B:
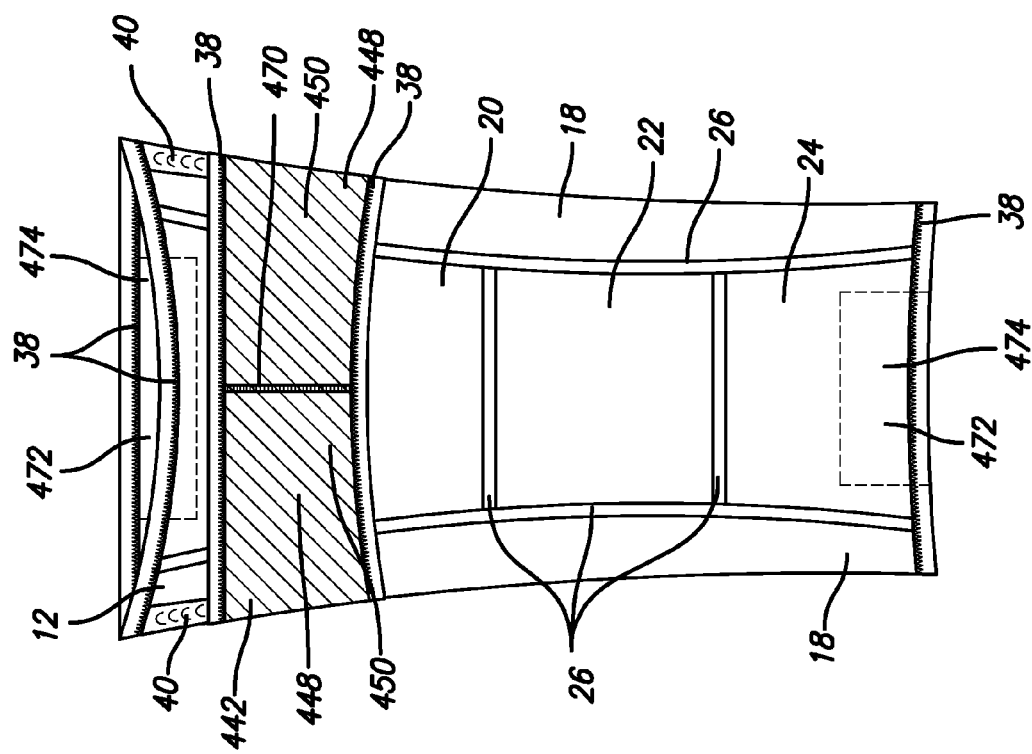
FIGS. 8(a)-8(b) present front and rear views, respectively, of the mesh support layer of FIGS. 7(a)-7(b) positioned on the base of FIGS. 1(a)-1(b)
Figure 8A:
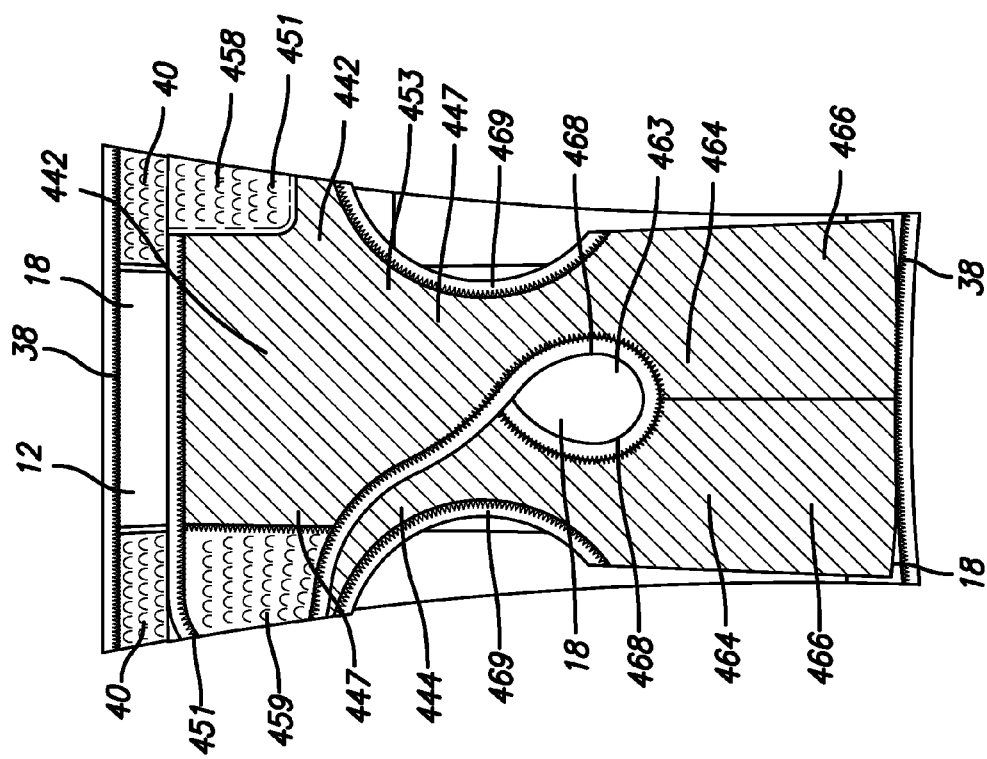

FIGS. 7(a)-7(b) present views of the outside (normally exposed) face 443 and the inside face 447, respectively, of an exemplary mesh support layer, indicated generally at 442, for use in a preferred embodiment of a knee brace according to the invention. FIGS. 8(a)-8(b) present front and rear views, respectively, of the mesh support layer 442 of FIGS. 7(a)-7(b) positioned on the base 12 of FIGS. 1(a)-1(b).

The mesh support layer 442 is preferably made of an elastic sheet material that is strong yet porous and lightweight, such as a polyester or nylon material. The mesh support layer 442 is preferably formed using a first (right) mesh support panel 444 and a second (left) mesh support panel 446 which are joined together, for example, by stitched seams 470. The mesh support layer 442 preferably includes an above-knee rear mesh strap 450 at the back of the thigh. The above-knee rear mesh strap 450 can be formed, for example, by including an above-knee rear mesh strap portion 448 on each of the first mesh support panel 444 and the second mesh support panel 446, and joining the two above-knee rear mesh strap portions 448 at the back of the thigh using stitched seams 470.

The inside face 447 of the mesh support panel 442 may include mesh support layer suspension fastening tabs 452 which are preferably formed of hook-type material of the type marketed under the trademark VELCRO. The fastening tabs 452 may be fastened to the mesh support panel 442 using stitches 451, although this is not required.

The mesh support layer 442 preferably also includes an above-knee closure assembly, indicated generally at 453, which is positioned at the front of the thigh during use. The above-knee closure assembly 453 can be formed, for example, using a right overlapping ear 454 formed as part of the right mesh support panel 444 and a left overlapping ear 456 formed as part of the second mesh support panel 446.

The outside face 443 of each of the right and left support panels 444, 446 preferably includes an ear middle fastening patch 458 formed of loop-type material of the type marketed under the trademark VELCRO. The outside face 443 of the end of each of the right and left overlapping ears 454, 456 may include an ear end fastening patch 459 formed of loop-type material of the type marketed under the trademark VELCRO. The inside face 443 of the end of each of the right and left overlapping ears 454, 456 may include an ear end fastening tab 460 formed of hook-type material of the type marketed under the trademark VELCRO.

After the base has been positioned on the knee of the wearer, the closure assembly 453 can be used to secure the brace on the knee. First, the right mesh overlapping ear 454 is wrapped around the front of the thigh to a desired level of tension. Then, the suspension fastening tab 452 and the ear end fastening tab 460 on that right ear 454 are pressed against corresponding suspension fastening patches 40 on the base 12, to detachably attach the right ear 454 to the base 12. Second, the left mesh overlapping ear 456 is wrapped around the front of the thigh, on top of the right mesh overlapping ear 454, to a desired level of tension. Then, the suspension fastening tab 452 and the ear end fastening tab 460 on that left ear 456 are pressed against the ear end fastening patch 459 and the ear middle fastening patch 458, respectively, on the right ear 454, to detachably attach the left ear 456 to the right ear 454 and the base 12.

Advantageously, the construction of the closure assembly 453 is symmetric with respect to the right and left overlapping ears 454, 456. Consequently, either the right or the left overlapping ear can be applied first, although the preceding discussion of the process for fastening the brace assumed that the right overlapping ear is applied first. No matter which ear is applied first, the front side mesh cutouts 468 of the mesh support 442 form a patella aperture 463 which encircles the kneecap when the brace is worn.

The mesh support 442 can include a patella strap mesh portion 464 as shown, for example, in FIG. 8(a) extending underneath the patella strap portion 478 of the below-knee support panel 476 shown in FIGS. 9(a)-9(d). The mesh support 442 can include a mesh anchor portion 466 extending vertically below the area of the kneecap when the brace is worn. The mesh support 442 can include overlapping ears 454, 456 that form a closure assembly 453 that encircles the kneecap. The mesh support 442 can have a symmetric construction, allowing either side of the mesh to be wrapped first.

The base 12 preferably includes one or more cuff reinforcements 472 at the upper and/or lower cuffs of the base. One or more non-slip patches 474 may also be provided on the inside of the upper and/or lower cuffs of the base to inhibit movement of the base on the leg during use.

FIGS. 9(a)-9(d) present front, rear, right side, and left side views, respectively, of a preferred embodiment of a knee brace according to the invention, indicated generally at 410, that includes the mesh support layer 442 and the base. The completed brace 410 adds a below-knee support panel, indicated generally at 476, and a below-knee rear strap closure assembly, indicated generally at 489, to the base and mesh support layer of FIGS. 8(*a*)-8(*b*).

The below-knee support panel 476 is preferably formed, for example, of a durable inelastic sheet material such as leather, sheet vinyl, synthetic suede, or the material sold under the trademark KEVLAR. The below-knee support panel 476 includes a patella strap panel portion 478, roughly semicircular in shape, and positioned above the patella tendon located vertically below the kneecap when the brace is worn on the leg of a person. The patella strap panel portion 478 extends from one support panel end 480 to another support panel end 480. The patella strap panel portion 478 covers a patella support member pocket 482 formed, for example, by stitched seams 470. A patella support member 484, for example a foam material or resilient plastic tubing, can be placed in the patella support member pocket 482.

The below-knee support panel 476 also includes a below-knee strap panel portion 486. The support panel 476 may also include a below-knee strap panel reinforcing pad 488. The brace 410 may also include a below-knee rear strap closure assembly 489. The below-knee rear strap closure assembly 489 preferably includes an outside elastic strap that has an elastic portion 490 and a fastening tab 492, and an inside elastic strap that has an elastic portion 494 and a fastening patch 496. The fastening tab 492 is preferably formed of hook type material and the fastening patch 496 is preferably formed of loop type material, so that they will adhere when pressed together.

FIGS. 10(*a*) and 10(*b*) present right side and left side views, respectively, of an alternative base 212 with mechanical hinges for use in an alternative embodiment of a knee brace according to the invention. FIG. 10(*a*) shows the first (right) side 214 of the base 212, while FIG. 10(*b*) shows the second (left) side 216 of the base 212. The construction of the alternative base 212 is for illustration only, and other constructions could be used in a knee brace according to the invention.

The base 212 includes a front panel 218 and is preferably made of, for example, an elastic sheet material such as polyester, spandex, or neoprene or other similar material suitable for use in an athletic brace. The rear of the base 212 is preferably, but not necessarily, formed of three panels, a rear upper panel 220, a rear central panel 222, and a rear lower panel 224. The front panel 218, rear upper panel 220, rear central panel 222, and rear lower panel 224 are preferably, but not necessarily, joined together using stitched seams 226. The base 212 may include edge binding 238 to finish any exposed edges, such as the cuffs of the base 212, although this is not required.

The base 212 preferably includes one or more upright support members 228 located on one or both sides of the base 212. Each upright support member 228 can be formed, for example, by placing a mechanical hinge 230 in an upright support pocket 232 formed using a side pocket cover strip 234 mounted to the side of the base 212 using stitches 236.

The base 212 also includes an upper mesh support suspension fastening patch 240 mounted to each upper side portion of the base 212. The upper mesh support fastening patch 240 is preferably made of a loop-type material of the type marketed under the trademark VELCRO.

FIG. 11 presents front and side views of an exemplary mechanical hinge 230 for use in an alternative embodiment of a knee brace according to the invention. The particular hinge shown in FIG. 11 is not required, and alternate hinges can be used, for example of the types shown in U.S. Pat. No. 4,726,362 to Nelson, or U.S. Pat. Nos. 4,573,455 or 4,844,057 to Hoy.

Figure 12B:
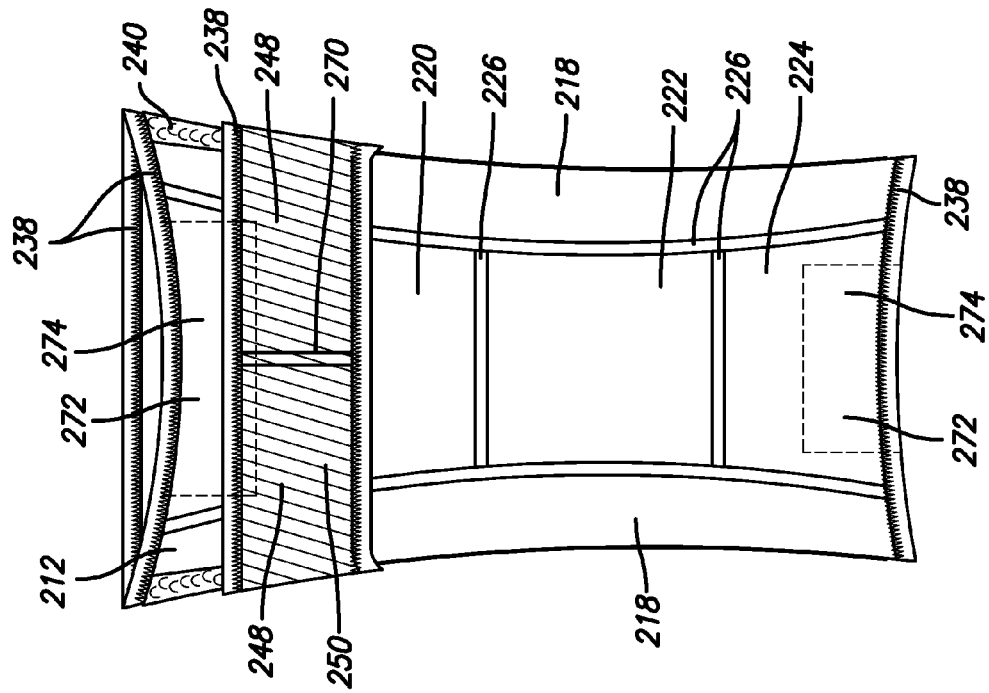
Figure 12A:
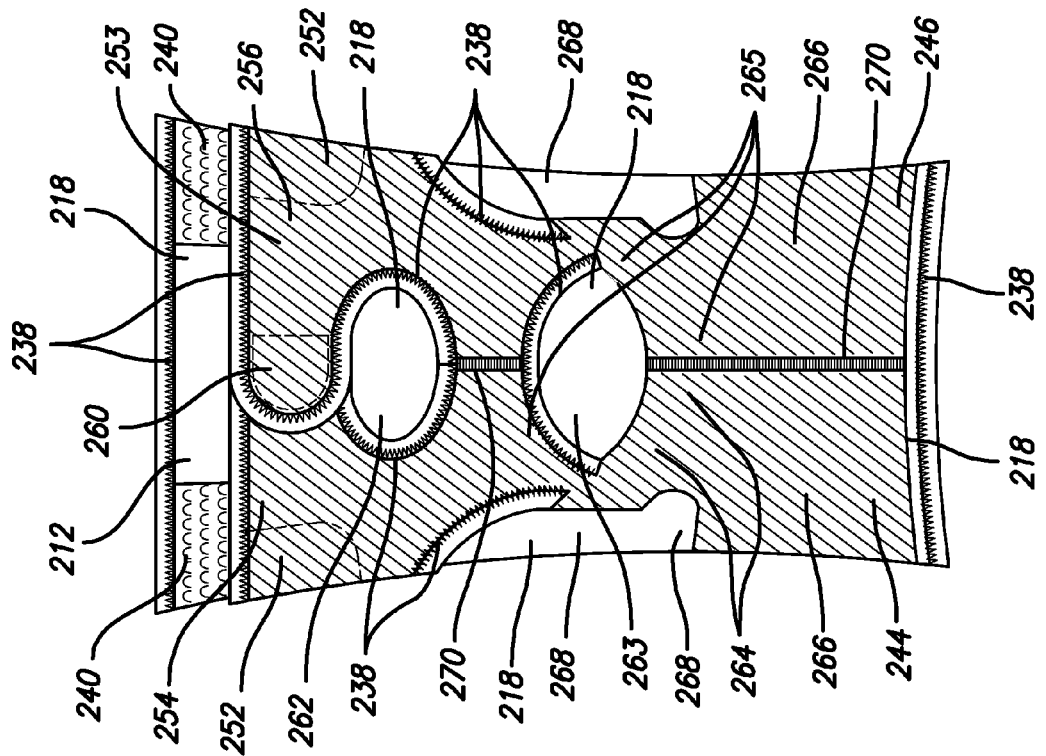

FIGS. 12(*a*)-12(*d*) present front, rear, right side, and left side views, respectively, of an exemplary mesh support layer, indicated generally at 242, for use in an alternative knee brace with mechanical hinges according to the invention. The mesh support layer 242 is preferably made of an elastic sheet material that is strong yet porous and lightweight, such as a polyester or nylon material. The mesh support layer 242 is preferably formed using a first (right) mesh support panel 244 and a second (left) mesh support panel 246 which are joined together, for example, by stitched seams 270.

The mesh support layer 242 preferably includes an above-knee rear mesh strap 250 at the back of the thigh. The above-knee rear mesh strap 250 can be formed, for example, by including an above-knee rear mesh strap portion 248 on each of the first mesh support panel 244 and the second mesh support panel 246, and joining the two above-knee rear mesh strap portions 248 at the back of the thigh using stitched seams 270.

The mesh support panel 242 preferably also includes a mesh support layer suspension fastening tab 252 which is preferably formed of hook-type material of the type marketed under the trademark VELCRO.

The mesh support layer 242 preferably also includes an above-knee front strap 253 at the front of the thigh. The above-knee front strap 253 can be formed, for example, using a right front strap portion 254 formed as part of the first mesh support panel 244 and a left front strap portion 256 formed as part of the second mesh support panel 246.

The right front strap portion 254 preferably includes a fastening patch 258 formed of loop-type material of the type marketed under the trademark VELCRO. The left front strap portion 256 preferably includes a fastening tab 260 which is preferably formed of hoop-type material of the type marketed under the trademark VELCRO. The right front strap portion 254 is detachably attachable to the left front strap portion 256 by pressing the fastening tab 260 against the fastening patch 258, to secure the above-knee front strap 253 around the thigh of the wearer of the brace.

The mesh support layer 242 preferably includes an above-knee aperture 262 between the above-knee front strap 253 and the lower portion of the brace.

The mesh support 242 can include a patella strap mesh portion 264 as shown, for example, in FIG. 12(*a*) extending underneath the patella strap portion 278 of the below-knee support panel 276 shown, for example, in FIG. 13(*a*). The mesh support 242 can include a patella support mesh portion 265 as shown, for example, in FIG. 12(*a*) encircling the kneecap when the brace is worn. The mesh support 242 can include a below-knee mesh portion 266 as shown, for example, in FIG. 12(*a*) positioned vertically below the area of the kneecap when the brace is worn.

The mesh support layer 242 is preferably attached to the sides of the base 212 using stitched seams 270.

The base 212 preferably includes one or more cuff reinforcements 272 at the upper and/or lower cuffs of the base. One or more non-slip patches 274 may also be provided on the inside of the upper and/or lower cuffs of the base to inhibit movement of the base on the leg during use.

FIGS. 13(*a*)-13(*d*) present front, rear, right side, and left side views, respectively, of an alternative knee brace according to the invention, indicated generally at 210, that includes the mesh support layer 242 of FIGS. 9(*a*)-9(*d*), with the mechanical hinges and hinge cover removed. The completed brace of FIGS. 13(*a*)-13(*d*) adds a below-knee support panel 276 and a below-knee elastic strap 290 to the base 212 and mesh support layer 242 of FIGS. 12(*a*)-12(*d*).

The below-knee support panel 276 is preferably formed, for example, of a durable inelastic sheet material such as leather, sheet vinyl, synthetic suede, or the material sold under the trademark KEVLAR. The below-knee support panel 276 includes a patella strap panel portion 278, roughly semicircular in shape, and positioned above the patella tendon located vertically below the kneecap when the brace is worn on the leg of a person. The patella strap panel portion 278 extends from one support panel end 280 to another support panel end 280. The patella strap panel portion 278 covers a patella support member pocket 282 formed, for example, by stitched seams 270. A patella support member 284 can be placed in the patella support member pocket 282.

The below-knee support panel 276 also includes a below-knee strap panel portion 286. The support panel 176 may include cutouts 288 on each side of the panel 276, for example so that the support panel can flex more readily below the patella strap panel portion 278 as the knee bends.

The brace 210 may also include a below-knee elastic strap 290. The below-knee elastic strap 290 extends from a first end 291 to a second end 293. The first end 291 is preferably permanently fixed to the base 212, the support panel 276, and or the edge of the mesh support 242, for example by sewing. The second end 293 is preferably not permanently fixed to the base 212 or support panel 276. Instead, the second end 293 of the below-knee elastic strap 290 preferably includes a fastening tab 294 formed of hook-type material of the type sold under the trademark VELCRO for releasable attachment to a below-knee strap fastening patch 292 secured to the below-knee support panel 276, for example by stitched seams 236.

Figure 15:
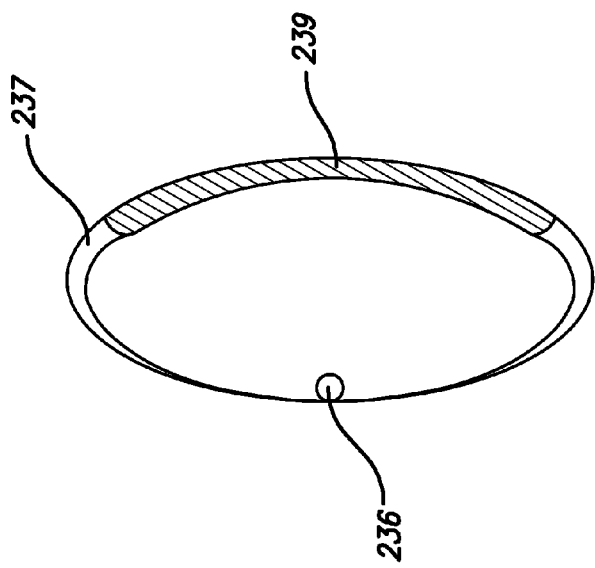
FIG. 15 presents a cross-sectional view of the hinge cover of FIG. 14, taken along the line 15-15 thereof.
Figure 14:
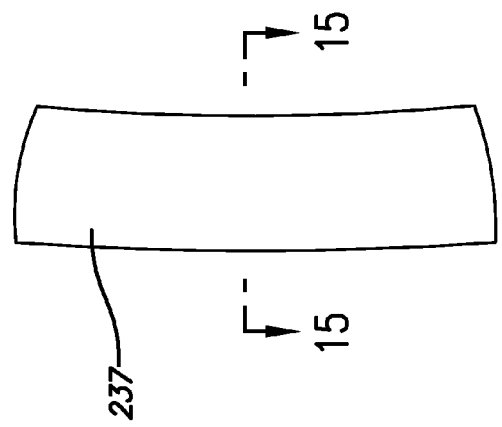
FIG. 14 presents a side view of an exemplary hinge cover for use in the knee brace of FIGS. 13(a)-13(d)

FIG. 14 presents a side view of an exemplary hinge cover 237 for use in the knee brace of FIGS. 13(a)-13(d). FIG. 15 presents a cross-sectional view of the hinge cover 237 of FIG. 14, taken along the line 15-15 thereof. The hinge cover 237 can be formed, for example, by forming a cylinder of flexible sheet material and sewing adjacent edges together with sewn seams 236. The hinge cover 237 preferably includes a layer of foam padding 239 on the outside layer of the hinge cover 237 for cushioning.

FIGS. 16(a)-16(d) present front, rear, right side, and left side views, respectively, of another exemplary mesh support layer, indicated generally at 342, for use in another alternative embodiment of a knee brace according to the invention. The mesh support layer 342 is preferably made of an elastic sheet material that is strong yet porous and lightweight, such as a polyester or nylon material. The mesh support layer 342 is preferably formed using a first (right) mesh support panel 344 and a second (left) mesh support panel 346 which are joined together, for example, by stitched seams 370.

The mesh support layer 342 preferably includes an above-knee rear mesh strap 350 at the back of the thigh. The above-knee rear mesh strap 350 can be formed, for example, by including an above-knee rear mesh strap portion 348 on each of the first mesh support panel 344 and the second mesh support panel 346, and joining the two above-knee rear mesh strap portions 348 at the back of the thigh using stitched seams 370.

The mesh support panel 342 preferably also includes a mesh support layer suspension fastening tab 352 which is preferably formed of hook-type material of the type marketed under the trademark VELCRO.

The mesh support layer 342 preferably also includes an above-knee front strap 353 at the front of the thigh. The above-knee front strap 353 can be formed, for example, using a right front strap portion 354 formed as part of the first mesh support panel 344 and a left front strap portion 356 formed as part of the second mesh support panel 346.

The right front strap portion 354 preferably includes a fastening patch 358 formed of loop-type material of the type marketed under the trademark VELCRO. The left front strap portion 356 preferably includes a fastening tab 360 which is preferably formed of hoop-type material of the type marketed under the trademark VELCRO. The right front strap portion 354 is detachably attachable to the left front strap portion 356 by pressing the fastening tab 360 against the fastening patch 358, to secure the above-knee front strap 353 around the thigh of the wearer of the brace.

The mesh support layer 342 preferably includes an above-knee aperture 362 between the above-knee front strap 353 and the lower portion of the brace.

Figure 16B:
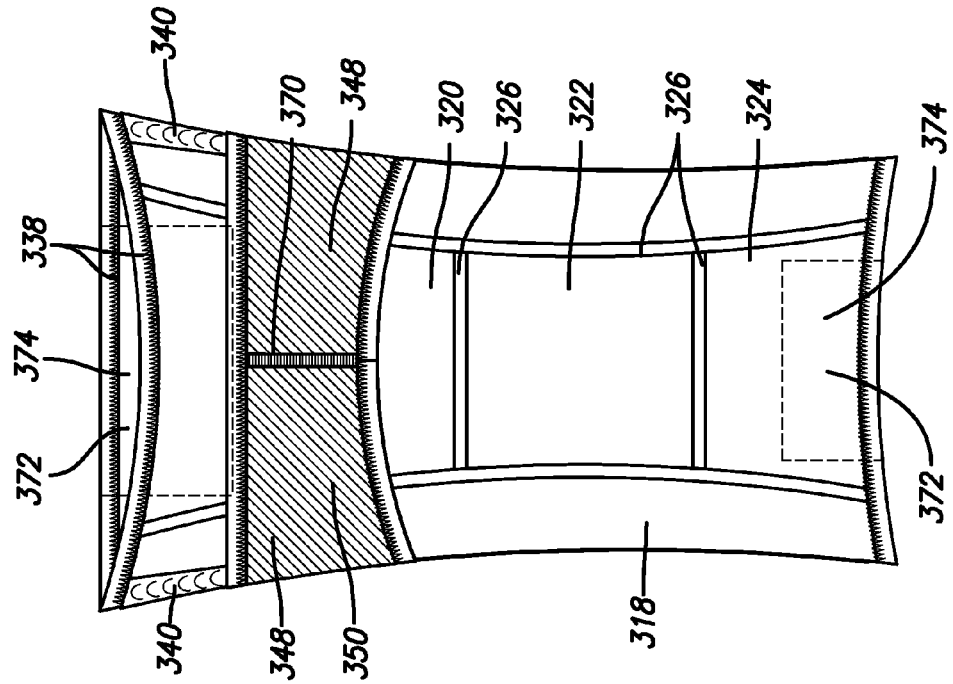
Figure 16A:
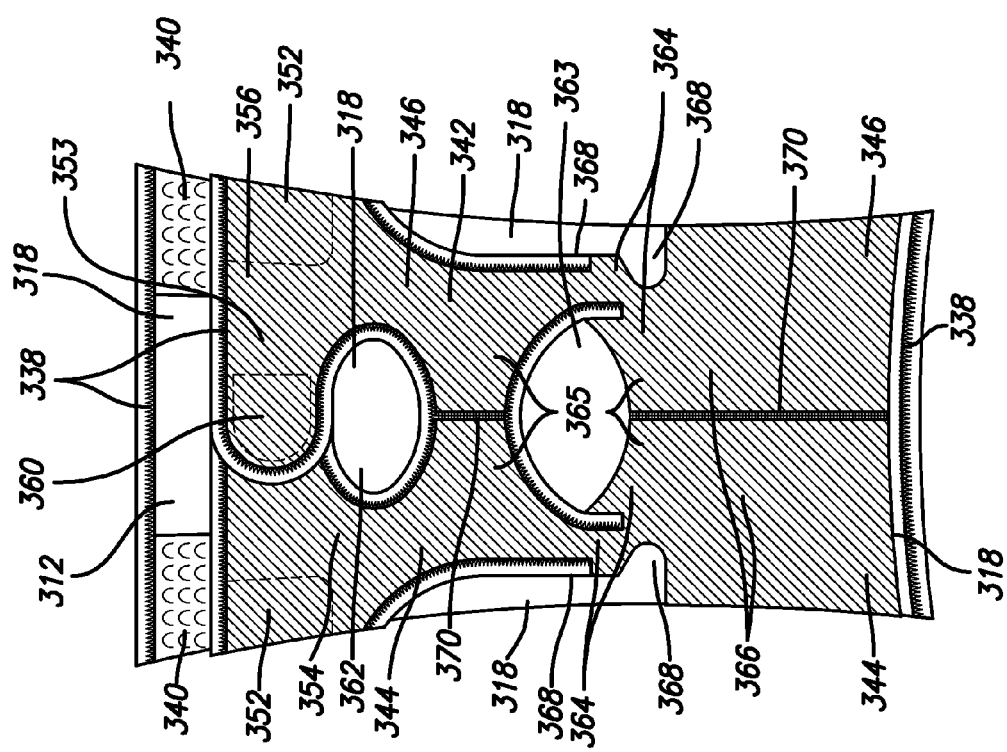

The mesh support 342 can include a patella strap mesh portion 364 as shown, for example, in FIG. 16(a) extending underneath the area of the patellar tendon when the brace is worn. The mesh support 342 can include a patella support mesh portion 365 as shown, for example, in FIG. 16(a) encircling the kneecap when the brace is worn. The mesh support 342 can include a below-knee mesh portion 366 as shown, for example, in FIG. 16(a) positioned vertically below the area of the kneecap when the brace is worn.

The mesh support layer 342 is preferably attached to the sides of the base 312 using stitched seams 370.

The base 312 preferably includes one or more cuff reinforcements 372 at the upper and/or lower cuffs of the base. One or more non-slip patches 374 may also be provided on the inside of the upper and/or lower cuffs of the base to inhibit movement of the base on the leg during use.

Figure 17A:
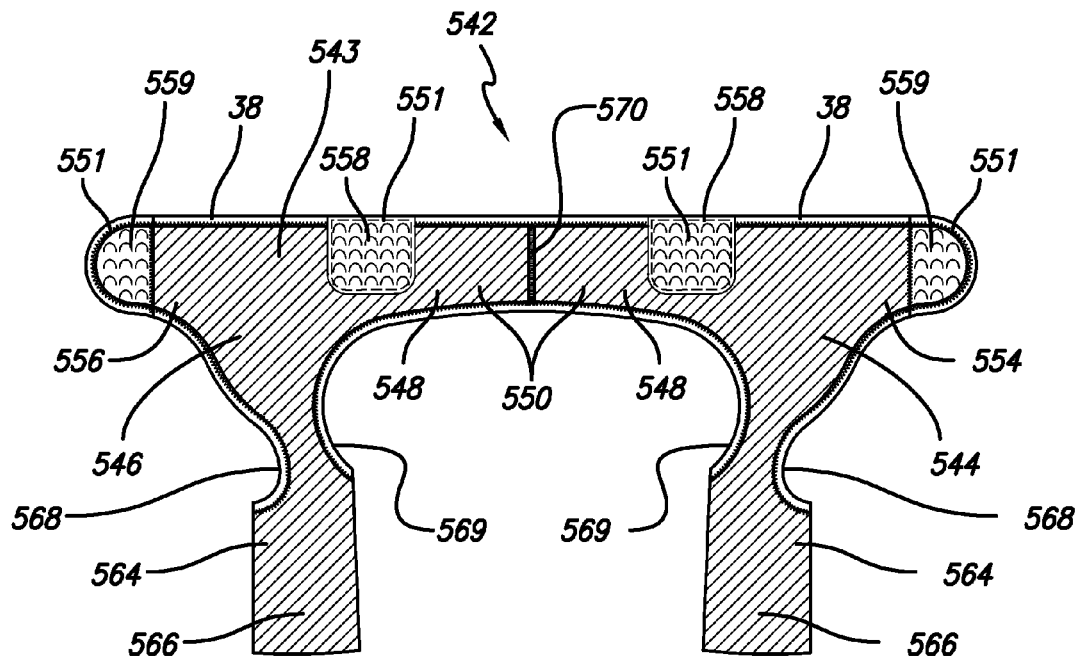
FIGS. 17(a)-17(b) present front and rear views, respectively, of an exemplary mesh support layer for use in an alternative knee brace according to the invention.
Figure 17B:
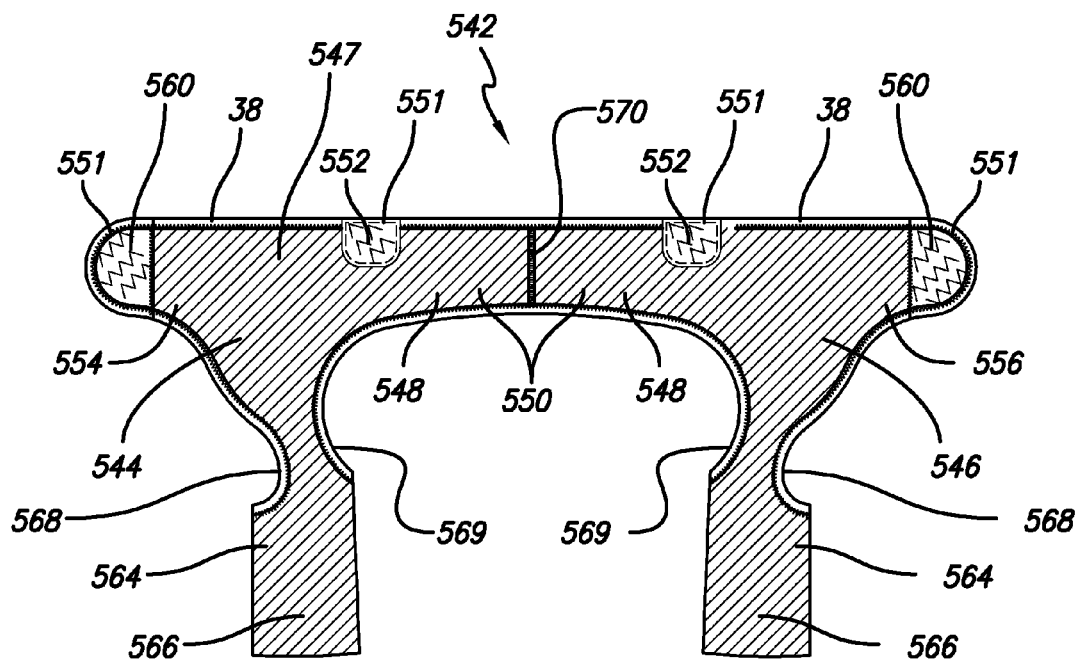
Figure 18B:
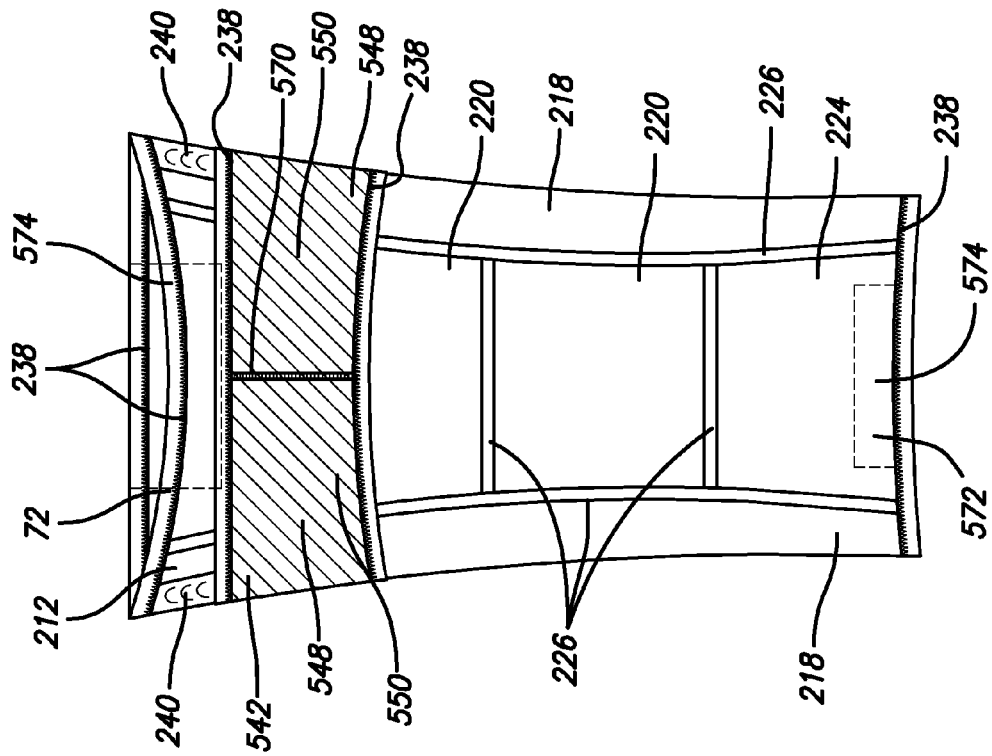
FIGS. 18(a)-18(b) present front and rear views, respectively, of the mesh support layer of FIGS. 17(a)-17(b) positioned on the base of FIG. 10.
Figure 18A:
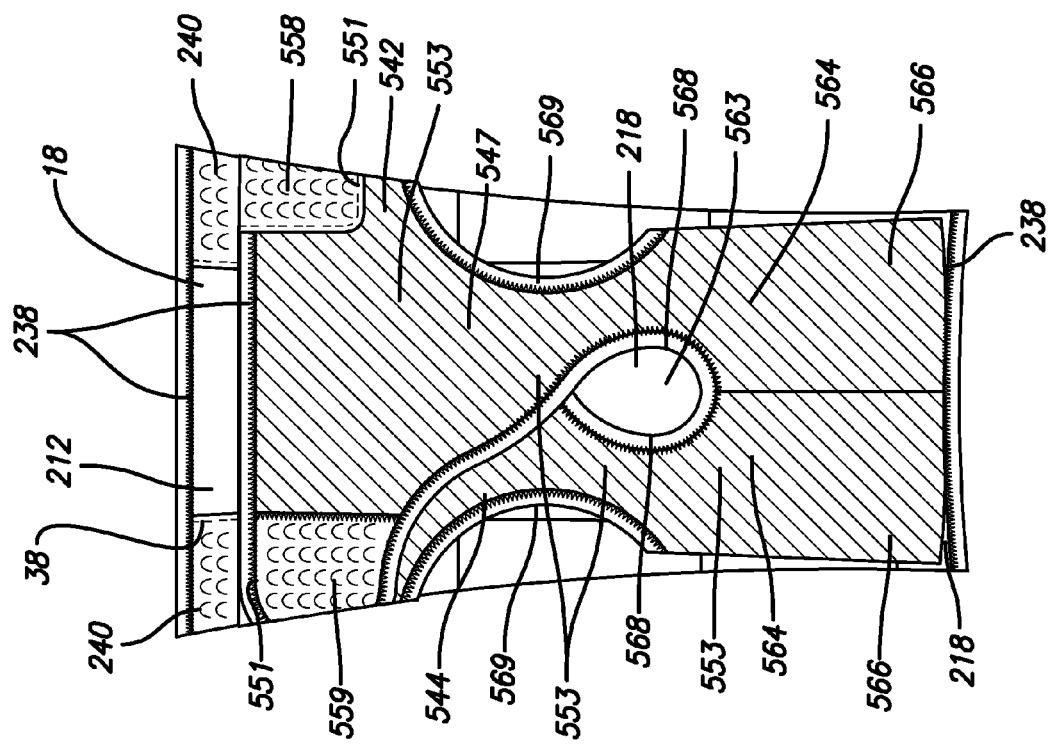

FIGS. 17(a)-17(b) present views of the outside (normally exposed) face 543 and the inside face 547, respectively, of an exemplary mesh support layer, indicated generally at 542, for use in a preferred embodiment of a knee brace according to the invention. FIGS. 18(a)-18(b) present front and rear views, respectively, of the mesh support layer 542 of FIGS. 17(a)-17(b) positioned on the base 212 of FIGS. 10(a)-10(b).

The mesh support layer 542 is preferably formed using a first (right) mesh support panel 544 and a second (left) mesh support panel 546 which are joined together, for example, by stitched seams 570. The mesh support layer 542 preferably includes an above-knee rear mesh strap 550 at the back of the thigh. The above-knee rear mesh strap 550 can be formed, for example, by including an above-knee rear mesh strap portion 548 on each of the first mesh support panel 544 and the second mesh support panel 546, and joining the two above-knee rear mesh strap portions 548 at the back of the thigh using stitched seams 570.

The inside face 547 of the mesh support panel 542 may include mesh support layer suspension fastening tabs 552 which are preferably formed of hook-type material of the type marketed under the trademark VELCRO. The fastening tabs 552 may be fastened to the mesh support panel 542 using stitches 551, although this is not required and other fasteners can be used.

The mesh support layer 542 preferably also includes an above-knee closure assembly, indicated generally at 553, which is positioned at the front of the thigh during use. The above-knee closure assembly 553 can be formed, for example, using a right overlapping ear 554 formed as part of the right mesh support panel 544 and a left overlapping ear 556 formed as part of the second mesh support panel 546.

The outside face 543 of each of the right and left support panels 544, 546 preferably includes an ear middle fastening patch 558 formed of loop-type material of the type marketed under the trademark VELCRO. The outside face 543 of the end of each of the right and left overlapping ears 554, 556 may include an ear end fastening patch 559 formed of loop-type material of the type marketed under the trademark VELCRO. The inside face 543 of the end of each of the right and left overlapping ears 554, 556 may include an ear end fastening tab 560 formed of hook-type material of the type marketed under the trademark VELCRO.

After the base has been positioned on the knee of the wearer, the closure assembly 553 can be used to secure the brace on the knee. First, the right mesh overlapping ear 554 is wrapped around the front of the thigh to a desired level of tension. Then, the suspension fastening tab 552 and the ear end fastening tab 560 on that right ear 554 are pressed against corresponding suspension fastening patches 240 on the base 212, to detachably attach the right ear 554 to the base 212. Second, the left mesh overlapping ear 556 is wrapped around the front of the thigh, on top of the right mesh overlapping ear 554, to a desired level of tension. Then, the suspension fastening tab 552 and the ear end fastening tab 560 on that left ear 556 are pressed against the ear end fastening patch 559 and the ear middle fastening patch 558, respectively, on the right ear 554, to detachably attach the left ear 556 to the right ear 554 and the base 212.

Advantageously, the construction of the closure assembly 553 is symmetric with respect to the right and left overlapping ears 554, 556. Consequently, either the right or the left overlapping ear can be applied first, although the preceding discussion of the process for fastening the brace assumed that the right overlapping ear is applied first. No matter which ear is applied first, the front side mesh cutouts 568 of the mesh support 542 form a patella aperture 563 which encircles the kneecap when the brace is worn.

The mesh support 542 can include a patella strap mesh portion 564 as shown, for example, in FIG. 18(*a*) extending underneath the patella strap portion 578 of the below-knee support panel 576 as shown, for example, in FIG. 19(*a*). The mesh support 542 can include a mesh anchor portion 566 as shown, for example, in FIG. 18(*a*) extending vertically below the area of the kneecap when the brace is worn. The mesh support 542 can include overlapping ears 554, 556 that form a closure assembly 553 as shown, for example, in FIG. 18(*a*) encircling the kneecap. The mesh support 542 can have a closure assembly with a symmetric construction, allowing either side of the mesh to be wrapped first.

The base 212 preferably includes one or more cuff reinforcements 572 at the upper and/or lower cuffs of the base. One or more non-slip patches 574 may also be provided on the inside of the upper and/or lower cuffs of the base to inhibit movement of the base on the leg during use.

FIGS. 19(*a*)-19(*d*) present front, rear, right side, and left side views, respectively, of an alternative knee brace according to the invention, indicated generally at 510, that includes the mesh support layer 542 and the base 212. The completed brace 510 adds a below-knee support panel 576 and a below-knee rear strap closure assembly 489 to the base 212 and mesh support layer 542.

The below-knee support panel 576 is preferably formed, for example, of a durable inelastic sheet material such as leather, sheet vinyl, synthetic suede, or the material sold under the trademark KEVLAR. The below-knee support panel 576 includes a patella strap panel portion 578, roughly semicircular in shape, and positioned above the patella tendon located vertically below the kneecap when the brace is worn on the leg of a person. The patella strap panel portion 578 extends from one support panel end 580 to another support panel end 580. The patella strap panel portion 578 covers a patella support member pocket 582 formed, for example, by stitched seams 570. A patella support member 584, for example a foam material or resilient plastic tubing, can be placed in the patella support member pocket 582.

The below-knee support panel 576 also includes a below-knee strap panel portion 586. The support panel 576 may also include a below-knee strap panel reinforcing pad 588.

The brace 510 may also include a below-knee rear strap closure assembly 589. The below-knee rear strap closure assembly 589 preferably includes an outside elastic strap that has an elastic portion 590 and a fastening tab 592, and an inside elastic strap that has an elastic portion 594 and a fastening patch 596. The fastening tab 592 is preferably formed of hook type material and the fastening patch 596 is preferably formed of loop type material, so that they will adhere when pressed together.

There are various possibilities with regard to alternative embodiments and methods including a knee brace according to the invention.

Although the preferred embodiments according to the invention disclosed herein include a base formed as a tubular sleeve, the base can also be formed as a reclosable sleeve.

The base may include a patella opening that generally matches the size of the patella, such that the patella (kneecap) of the wearer extends from the patella opening when the brace is worn, although this is not necessary. In addition to providing direct patella stabilization, the patella opening may help to locate the brace with respect to the patella during application of the brace. The patella opening, if present, could have a variety of shapes, e.g. circular, square, rectangular, elliptical, diamond, trapezoidal, or any substantial equivalent.

The base may include an opening, for example a circular aperture, over the popliteal area (the area at the rear of the knee), although this is not necessary. Such a popliteal opening can decrease the chance of irritation of the skin in that area. The popliteal opening, if present, could have a variety of shapes, e.g. circular, square, rectangular, elliptical, diamond, trapezoidal, or any substantial equivalent.

Although hook and loop type fastener material is preferably used to fasten the mesh support to the base, and to secure the upper and lower straps, equivalent fasteners such as zippers, clasps, buckles, pins, laces, or buttons may be substituted for the hook and loop type fastener material.

Although various components in the exemplary embodiments disclosed herein are preferably fastened together using stitches, this is not required. For example, other means such as glue, thermal bonding, or other substantial equivalents could be used.

There may be only a single upright support assembly on one side only of a knee brace according to the invention, there can be multiple upright support assemblies on one or both sides of a knee brace according to the invention. The elongated side pockets can be openable at one end to allow removal of the upright support members (the resilient stays or hinges), so that the brace may be washed or so that different upright support members may be inserted to adjust the amount and type of support provided.

Although the various embodiments of a mesh support according to the invention include ears with outside faces bearing separate middle and end fastening patches, a continuous strip of the loop material used for the fastening patches could be used instead. Although the various embodiments of a base according to the invention include separate mesh support fastening patches on each side, a continuous strip of the loop material used for the fastening patches could be used across the entire front of the base instead of separate patches. Although the various embodiments of a mesh support according to the invention include ears with inside faces bearing separate suspension and end fastening tabs, a continuous strip of the hook material used for the fastening tabs could be used instead.

It is understood that the invention is not confined to the embodiments set forth herein as illustrative, but embraces all such forms thereof that come within the scope of the following claims.

What is claimed is:

1. A knee brace, comprising:
   a base made of an elastic sheet material and wearable in snug covering relationship to the knee and adjacent portions of the upper leg and the lower leg of a person, the base having front, side and rear portions when the brace is worn, the base having an upper portion above the knee and a lower portion below the knee, whereby the upper portion of the base has a level of tension when the brace is worn;
   a mesh support layer made of an elastic mesh sheet material and having an upper portion that covers at least a part of the upper portion of the base and having a lower portion fixed to the lower portion of the base and extending below the knee when the brace is worn;
   wherein the upper portion of the mesh support layer is substantially separable from the upper portion of the base,
   whereby the upper portion of the mesh support layer has a level of tension that is adjustable substantially independently of the level of tension of the upper portion of the base when the brace is worn; and
   a below-knee support panel made of an inelastic sheet material fixed to the lower portion of the base, extending below the knee when the brace is worn, and covering at least a part of the lower portion of the base.

2. The knee brace of claim 1 further comprising one or more upright support members located on a side portion of the base.

3. The knee brace of claim 2 wherein at least one upright support member includes at least one elongated pocket and at least one resilient stay located in the elongated pocket.

4. The knee brace of claim 2 wherein at least one upright support member includes an upper upright support pocket, a lower upright support pocket, and a mechanical hinge having a first end that fits in the upper upright support pocket and a second end that fits in the lower upright support pocket.

5. The knee brace of claim 1 wherein at least half of the lower portion of the mesh support layer is positioned between the below-knee support panel and the base.

6. The knee brace of claim 1 wherein the upper portion of the mesh support layer includes an above-knee rear mesh strap and an above-knee front strap.

7. The knee brace of claim 6 wherein the above-knee front strap comprises a first strap portion having a fastening tab and a second strap portion having a fastening patch,
   whereby the fastening tab of the first strap portion can be releasably fastened to the fastening patch of the second strap portion to tighten the above-knee front strap about the upper leg of the wearer.

8. The knee brace of claim 1 wherein the upper portion of the mesh support layer includes at least one suspension tab, and wherein the base includes at least one suspension patch,
   whereby the suspension tab of the upper portion of the mesh support layer can be releasably fastened to the suspension patch of the base to position the upper portion of the mesh support layer on the base.

9. The knee brace of claim 1 further comprising a below-knee strap having a first end fixed to a portion of the base and a second end having a fastening tab; and
   further comprising a below-knee strap fastening patch fixed to one of the lower portion of the base, the lower portion of the mesh support layer, and the below knee support panel;
   whereby the fastening tab of the second end of the below-knee strap can be releasably fastened to the below-knee strap fastening patch to tighten the below-knee strap about the lower leg of the wearer.

10. The knee brace of claim 1 wherein the mesh support layer includes a closure assembly having a right ear and a left ear that are adapted to be fastened together at least two points.

11. The knee brace of claim 1 wherein the upper portion of the mesh support layer includes an above-knee rear mesh strap and an above-knee front closure assembly having overlapping ears.

12. The knee brace of claim 1 wherein the upper portion of the mesh support layer includes an above-knee rear mesh strap and an above-knee front closure assembly having two ears and a symmetric construction.

13. The knee brace of claim 1 further comprising a below-knee rear strap closure assembly.

14. The knee brace of claim 1 wherein the mesh support layer includes a closure assembly having a right ear and a left ear, each ear having an inside face with a middle bearing a suspension fastening tab and an end bearing an end fastening fab, and each ear having an outside face with a middle bearing a middle fastening patch and an end bearing an end fastening patch.

15. A knee brace, comprising:
   a base made of an elastic sheet material and wearable in snug covering relationship to the patella tendon and portions of the upper leg and the lower leg of a person, the base having front, side and rear portions when the brace is worn, the base having an upper portion above the knee and a lower portion below the knee, whereby the upper portion of the base has a position when the brace is worn;
   a mesh support layer made of an elastic mesh sheet material and having an upper portion that covers at least a part of the upper portion of the base and having a lower portion fixed to the lower portion of the base wherein the lower portion includes a patella strap portion that extends over at least the patella tendon when the brace is worn;
      wherein the upper portion of the mesh support layer is substantially separable from the upper portion of the base, whereby the upper portion of the mesh support layer around the leg has a position that is adjustable relative to the position of the upper portion of the base when the brace is worn; and
   a below-knee support panel made of an inelastic sheet material fixed to the lower portion of the base, extending below the knee when the brace is worn, and covering at least a part of the lower portion of the base.

16. The knee brace of claim 15 further comprising one or more upright support members located on a side portion of the base.

17. The knee brace of claim 15 wherein the patella strap portion of the lower portion of the mesh support layer is positioned between the below-knee support panel and the base.

18. The knee brace of claim 15 wherein the upper portion of the mesh support layer includes an above-knee rear mesh strap, and an above-knee front strap comprising a first strap portion having a fastening tab and a second strap portion having a fastening patch, whereby the fastening tab of the first strap portion can be releasably fastened to the fastening patch of the second strap portion to tighten the above-knee front strap about the upper leg of the wearer.

19. The knee brace of claim 15 wherein the upper portion of the mesh support layer includes at least one suspension tab, and wherein the base includes at least one suspension patch,
whereby the suspension tab of the upper portion of the mesh support layer can be releasably fastened to the suspension patch of the base to position the upper portion of the mesh support layer on the base.

20. The knee brace of claim 15 further comprising a below-knee strap having a first end fixed to a portion of the base and a second end having a fastening tab; and
further comprising a below-knee strap fastening patch fixed to one of the lower portion of the base, the lower portion of the mesh support layer, and the below knee support panel;
whereby the fastening tab of the second end of the below-knee strap can be releasably fastened to the below-knee strap fastening patch to tighten the below-knee strap about the lower leg of the wearer.

21. The knee brace of claim 15 wherein the mesh support layer includes a closure assembly having a right ear and a left ear that are adapted to be fastened together at least two points.

22. The knee brace of claim 15 wherein the upper portion of the mesh support layer includes an above-knee rear mesh strap and an above-knee front closure assembly having overlapping ears.

23. The knee brace of claim 15 wherein the upper portion of the mesh support layer includes an above-knee rear mesh strap and an above-knee front closure assembly having two ears and a symmetric construction.

24. The knee brace of claim 15 further comprising a below-knee rear strap closure assembly.

25. The knee brace of claim 15 wherein the mesh support layer includes a closure assembly having a right ear and a left ear, each ear having an inside face with a middle bearing a suspension fastening tab and an end bearing an end fastening fab, and each ear having an outside face with a middle bearing a middle fastening patch and an end bearing an end fastening patch.

26. The knee brace of claim 15 wherein the upper portion of the mesh support layer includes at least two suspension tabs, and wherein the base includes at least one suspension patch,
whereby each suspension tab of the upper portion of the mesh support layer can be releasably fastened to at least one suspension patch of the base to position the upper portion of the mesh support layer on the base.

27. A knee brace, comprising:
a base made of an elastic sheet material and wearable in snug covering relationship to the area surrounding the kneecap and portions of the upper leg and the lower leg of a person, the base having front, side and rear portions when the brace is worn, the base having an upper portion above the knee and a lower portion below the knee, whereby the upper portion of the base has a level of tension and a position when the brace is worn;
a mesh support layer made of an elastic mesh sheet material, having an upper portion that covers at least a part of the upper portion of the base, having a lower portion fixed to the lower portion of the base, and wherein the mesh support layer includes a patella support portion covering the area surrounding the kneecap, whereby the patella support portion encircles the kneecap when the brace is worn;
wherein the upper portion of the mesh support layer is substantially separable from the upper portion of the base, whereby the upper portion of the mesh support layer has a level of tension that is adjustable substantially independently of the level of tension of the upper portion of the base when the brace is worn, and whereby the upper portion of the mesh support layer has a position that is adjustable relative to the position of the upper portion of the base when the brace is worn; and
a below-knee support panel made of an inelastic sheet material fixed to the lower portion of the base, extending below the knee when the brace is worn, and covering at least a part of the lower portion of the base.

28. The knee brace of claim 27 further comprising one or more upright support members located on a side portion of the base.

29. The knee brace of claim 27 wherein the patella support portion of the mesh support layer is positioned between the below-knee support panel and the base.

30. The knee brace of claim 27 wherein the upper portion of the mesh support layer includes at least one suspension tab, and wherein the base includes at least one suspension patch,
whereby the suspension tab of the upper portion of the mesh support layer can be releasably fastened to the suspension patch of the base to position the upper portion of the mesh support layer on the base.

31. The knee brace of claim 27 further comprising a below-knee strap having a first end fixed to a portion of the base and a second end having a fastening tab; and
further comprising a below-knee strap fastening patch fixed to one of the lower portion of the base, the lower portion of the mesh support layer, and the below knee support panel;
whereby the fastening tab of the second end of the below-knee strap can be releasably fastened to the below-knee strap fastening patch to tighten the below-knee strap about the lower leg of the wearer.

* * * * *